(12) United States Patent
Zerhusen

(10) Patent No.: US 9,827,156 B2
(45) Date of Patent: Nov. 28, 2017

(54) PERSON SUPPORT APPARATUS

(71) Applicant: Hill-Rom Services, Inc., Batesville, IN (US)

(72) Inventor: Robert Mark Zerhusen, Cincinnati, OH (US)

(73) Assignee: Hill-Rom Services, Inc., Batesville, IN (US)

( * ) Notice: Subject to any disclaimer, the term of this patent is extended or adjusted under 35 U.S.C. 154(b) by 0 days.

(21) Appl. No.: 14/356,041

(22) PCT Filed: Nov. 12, 2012

(86) PCT No.: PCT/US2012/064692
§ 371 (c)(1),
(2) Date: May 2, 2014

(87) PCT Pub. No.: WO2013/071246
PCT Pub. Date: May 16, 2013

(65) Prior Publication Data
US 2014/0292529 A1 Oct. 2, 2014

Related U.S. Application Data

(60) Provisional application No. 61/559,035, filed on Nov. 11, 2011.

(51) Int. Cl.
*G08B 5/00* (2006.01)
*A61G 7/05* (2006.01)
(Continued)

(52) U.S. Cl.
CPC ............. *A61G 7/05* (2013.01); *A61G 7/0514* (2016.11); *A61G 7/0516* (2016.11); *A61G 7/0528* (2016.11); *A61G 12/00* (2013.01); *G06F 19/3406* (2013.01); *G08B 5/00* (2013.01); *A61G 7/012* (2013.01); *A61G 7/015* (2013.01); *A61G 7/018* (2013.01); *A61G 7/053* (2013.01); *A61G 7/0506* (2013.01); *A61G 2200/16* (2013.01); *A61G 2203/12* (2013.01); *A61G 2203/70* (2013.01); *A61G 2203/72* (2013.01)

(58) Field of Classification Search
CPC ......... G08B 5/00; G06F 19/3406; A61G 7/05; A61G 7/012
USPC ..................................................... 340/815.65
See application file for complete search history.

(56) References Cited

U.S. PATENT DOCUMENTS

| | | | | |
|---|---|---|---|---|
| 4,947,298 A | * | 8/1990 | Stephen | 362/130 |
| 6,234,642 B1 | * | 5/2001 | Bokamper | 362/130 |

(Continued)

*Primary Examiner* — Hai Phan
*Assistant Examiner* — Royit Yu
(74) *Attorney, Agent, or Firm* — Barnes & Thornburg LLP

(57) ABSTRACT

A person support apparatus with an extendable mattress, a night light message display system, a screen key pendant, egress handle siderails, and various other features. The extendable mattress includes hinged extensions along the sides of the extendable mattress that are moved from a nested position to the extension position. The screen key pendant includes a plurality of screen keys that can be pressed to cycle through various control modes for the person support apparatus. The night light message display system can be configured to display a message or image on the floor communicating information to the person and/or alerting the person as to when they are able to exit the bed.

19 Claims, 48 Drawing Sheets

(51) Int. Cl.
*A61G 12/00* (2006.01)
*G06F 19/00* (2011.01)
*A61G 7/012* (2006.01)
*A61G 7/015* (2006.01)
*A61G 7/018* (2006.01)
*A61G 7/053* (2006.01)

(56) References Cited

U.S. PATENT DOCUMENTS

| | | | |
|---|---|---|---|
| 7,033,028 B1* | 4/2006 | Belliveau | 353/31 |
| 7,874,695 B2* | 1/2011 | Jensen | 362/130 |
| 2002/0066142 A1* | 6/2002 | Osborne | A61G 7/005 5/600 |
| 2003/0052787 A1* | 3/2003 | Zerhusen et al. | 340/573.1 |
| 2008/0289108 A1* | 11/2008 | Menkedick et al. | 5/610 |
| 2010/0287703 A1* | 11/2010 | Zapata | 5/601 |
| 2011/0010854 A1* | 1/2011 | Zerhusen et al. | 5/425 |
| 2011/0119940 A1* | 5/2011 | Zerhusen | 33/333 |
| 2011/0157486 A1* | 6/2011 | Murata et al. | 348/744 |
| 2011/0169653 A1* | 7/2011 | Wang et al. | 340/686.6 |
| 2011/0234411 A1* | 9/2011 | Harrington et al. | 340/573.4 |
| 2012/0046100 A1* | 2/2012 | Roman et al. | 463/30 |
| 2012/0194356 A1* | 8/2012 | Haines et al. | 340/933 |

* cited by examiner

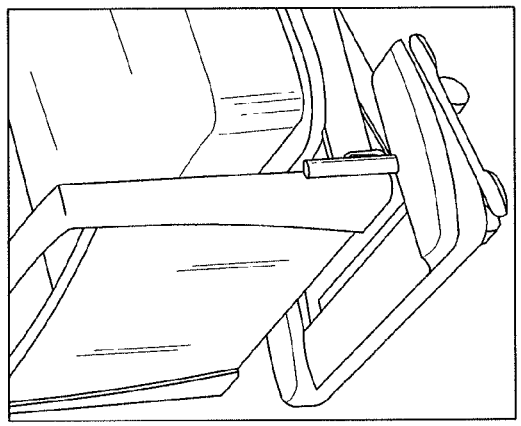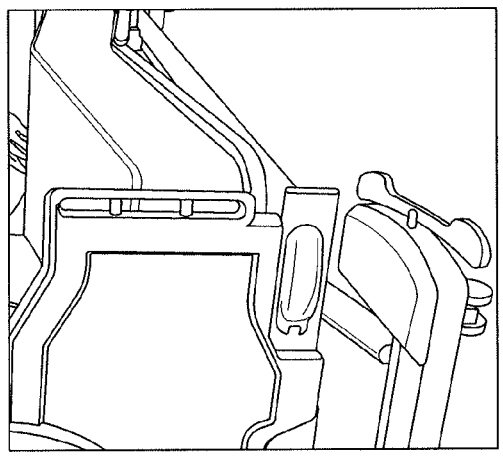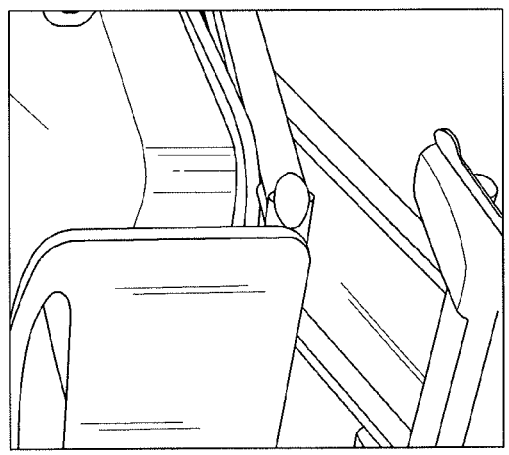
FIG. 21

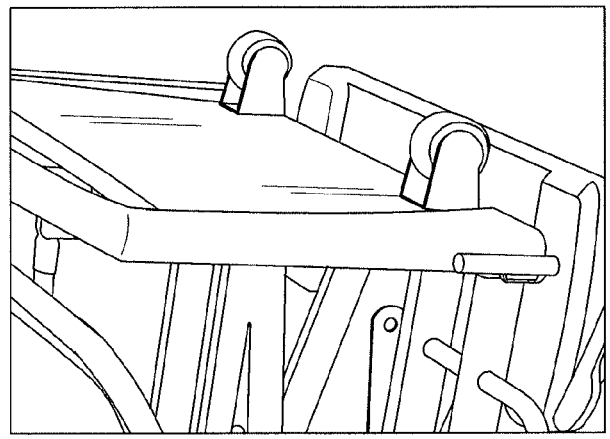
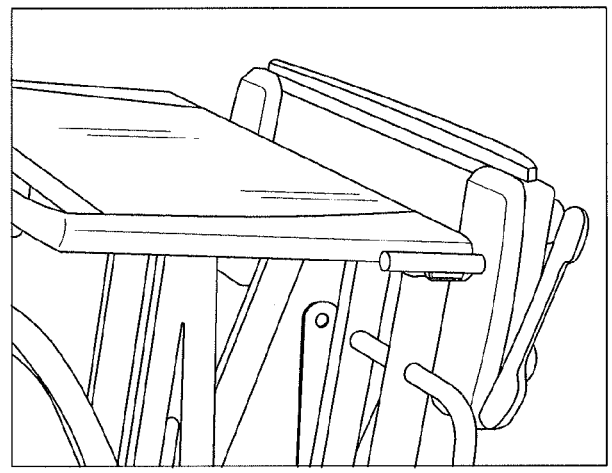
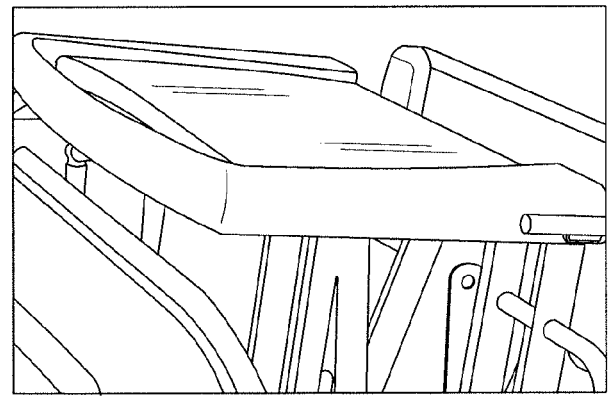
FIG. 22

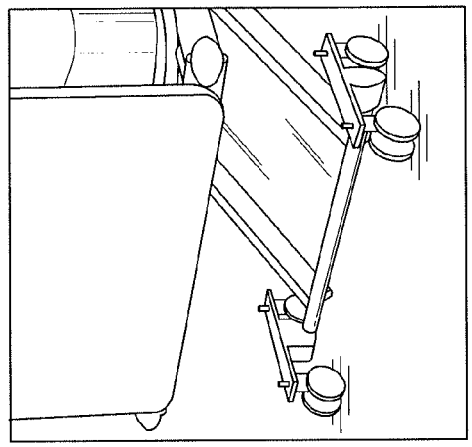
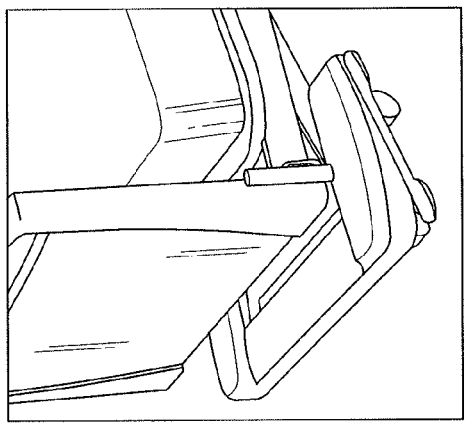
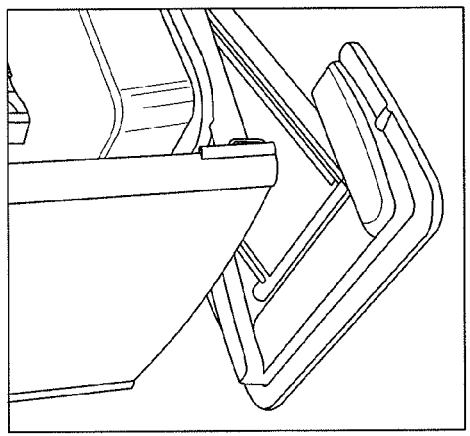
FIG. 23

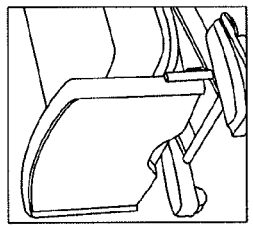 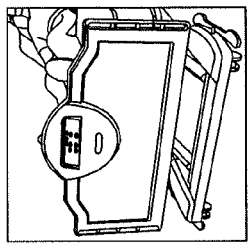 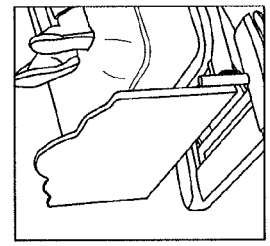
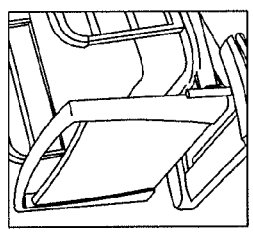 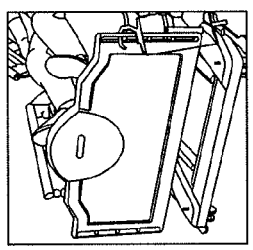 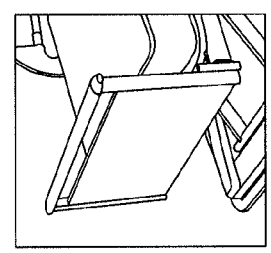
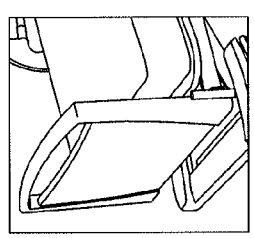 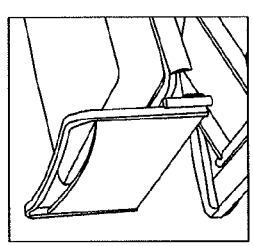 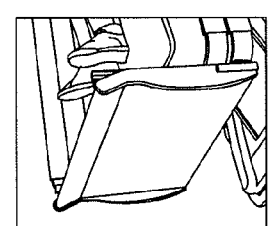
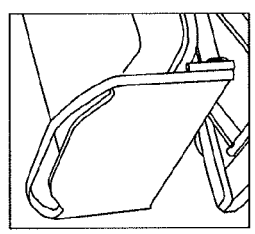 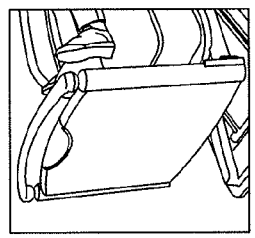 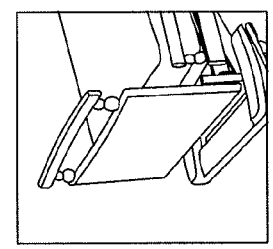
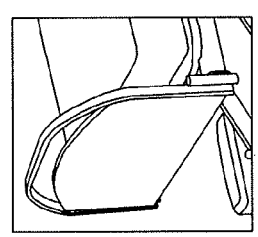 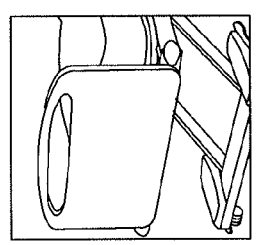 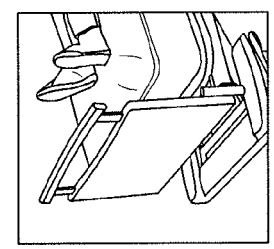
FIG. 41

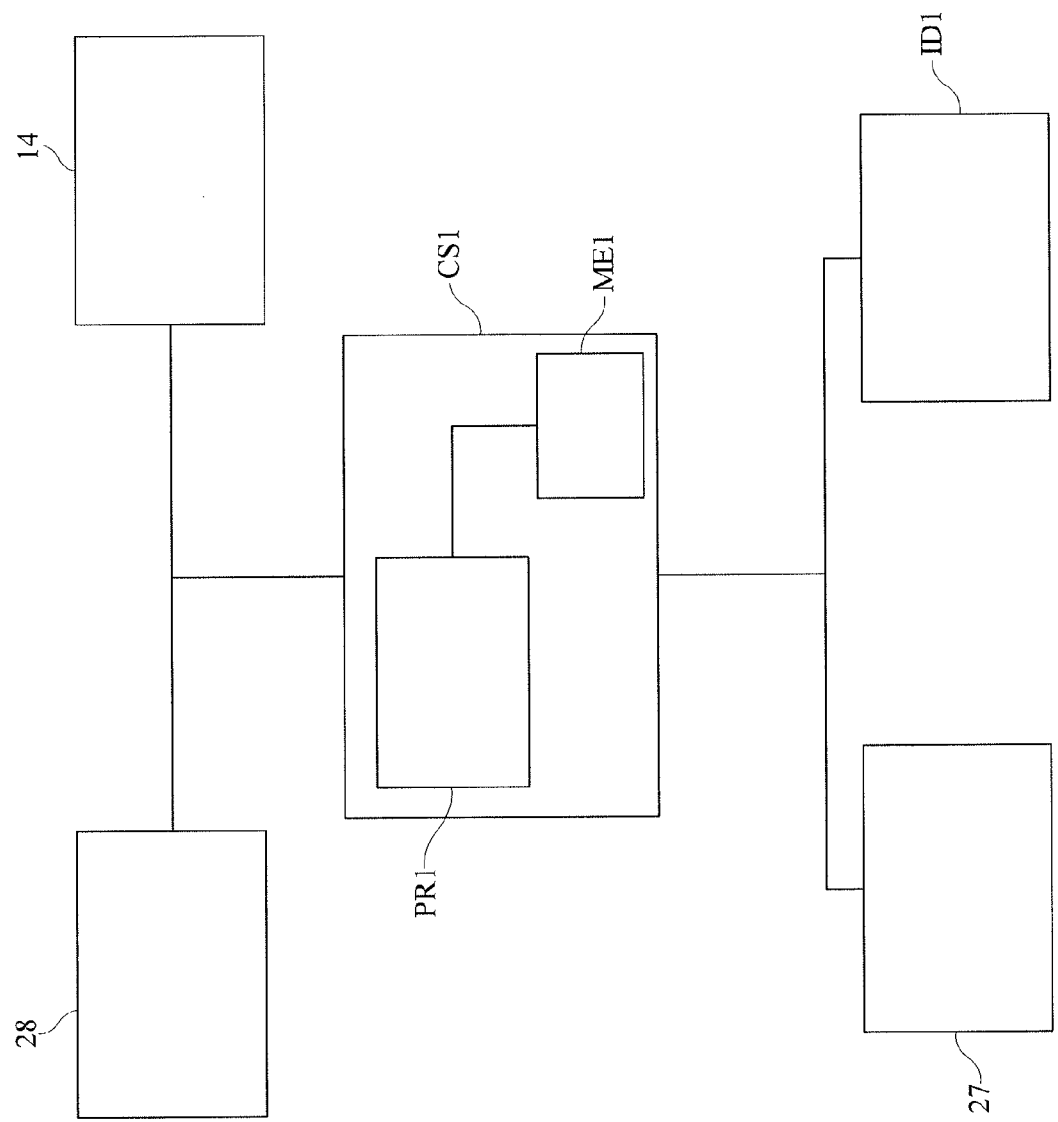

PERSON SUPPORT APPARATUS

CROSS REFERENCE TO RELATED APPLICATIONS

This Application claims priority to U.S. Provisional Application Ser. No. 61/559,035 titled PERSON SUPPORT APPARATUS filed on Nov. 11, 2011, the contents of which are incorporated herein by reference.

BACKGROUND OF THE DISCLOSURE

This disclosure relates particularly, but not exclusively, to person support apparatuses. While various person support apparatuses have been developed, there is still room for improvement. Thus a need persists for further contributions in this area of technology.

SUMMARY OF THE DISCLOSURE

In one illustrative embodiment, a mattress includes hinged extensions along the sides of the mattress that are moved from a nested position to the extension position. In another illustrative embodiment, the pendant includes a plurality of screen keys that can be pressed to cycle through various control modes for the person support apparatus. In another illustrative embodiment, a night light system can be configured to display a message or image on the floor communicating information to the person and/or alerting the person as to when they are able to exit the bed.

Additional features alone or in combination with any other feature(s), including those listed above and those listed in the claims and those described in detail below, can comprise patentable subject matter. Others will become apparent to those skilled in the art upon consideration of the following detailed description of illustrative embodiments exemplifying the best mode of carrying out the invention as presently perceived.

BRIEF DESCRIPTION OF THE DRAWINGS

Referring now to the illustrative examples in the drawings, wherein like numerals represent the same or similar elements throughout:

FIG. 21 is the status indicating lights of FIG. 20 according to another contemplated embodiment of the current disclosure;

FIG. 22 is a person support apparatus according to another contemplated embodiment of the current disclosure;

FIG. 23 is a person support apparatus according to another contemplated embodiment of the current disclosure;

FIG. 41 is a person support apparatus according to another contemplated embodiment of the current disclosure showing different configurations of endboards;

FIG. 48 is a person support apparatus according to another contemplated embodiment of the current disclosure showing the control system.

DETAILED DESCRIPTION OF THE DRAWINGS

Figure 1:
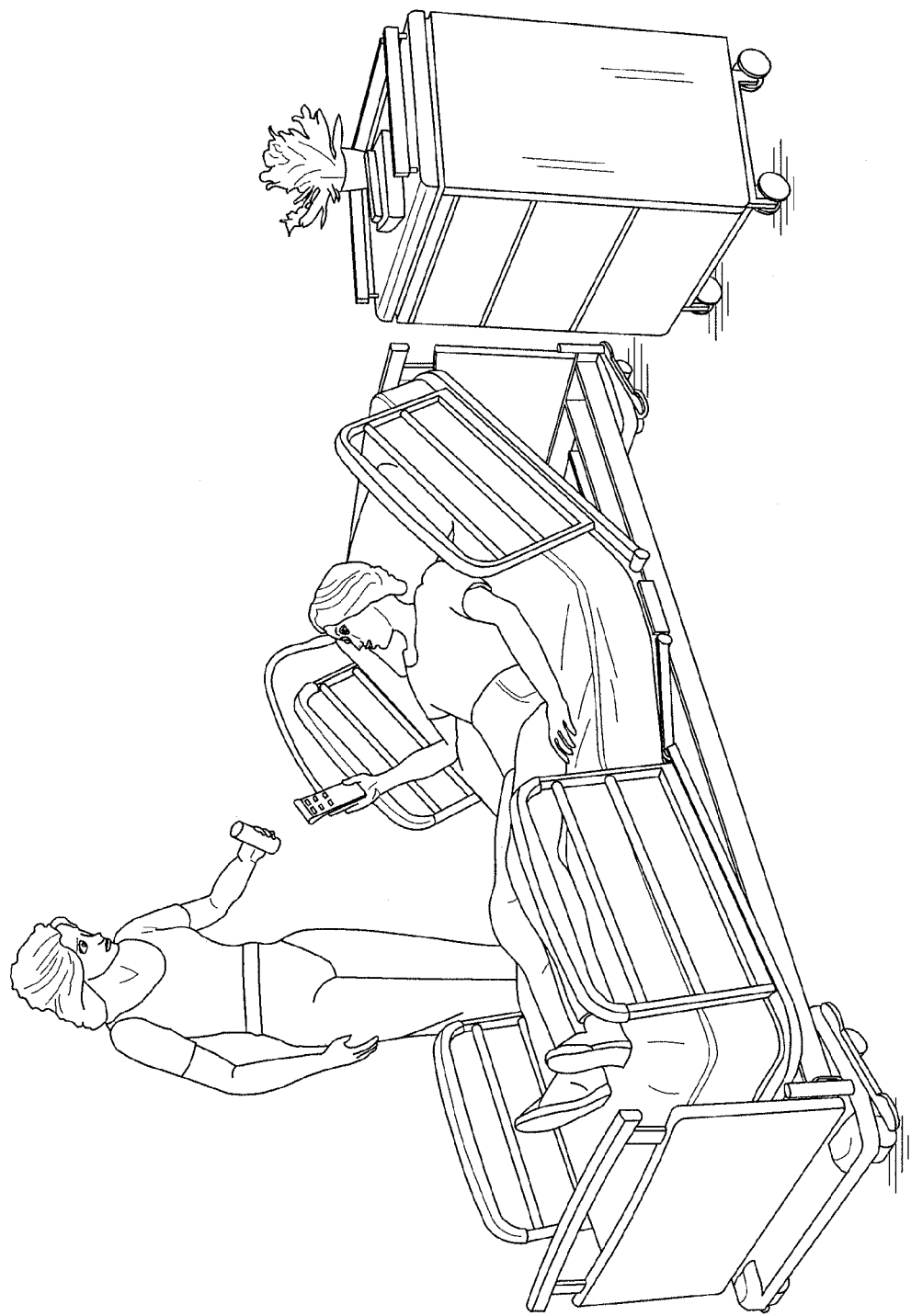
FIG. 1 is a person support apparatus according to one contemplated embodiment of the current disclosure showing the upper frame in a in a low reclined position with a pendant holder attached to the head section.

While the present disclosure can take many different forms, for the purpose of promoting an understanding of the principles of the disclosure, reference will now be made to the embodiments illustrated in the drawings, and specific language will be used to describe the same. No limitation of the scope of the disclosure is thereby intended. Various alterations, further modifications of the described embodiments, and any further applications of the principles of the disclosure, as described herein, are contemplated.

A person support apparatus 10 according to one illustrative embodiment of the current disclosure is shown in FIGS. 1-47. The person support apparatus 10 is a hospital bed with a first section F1 or head support section F1, where the head of a person (not shown) can be positioned and a second section S1 or a foot support section S1, where the feet of the person (not shown) can be positioned. In other contemplated embodiments, the person support apparatus 10 can be a hospital stretcher, an operating table, a wheelchair, or other apparatus configured to support a person.

Figure 2:
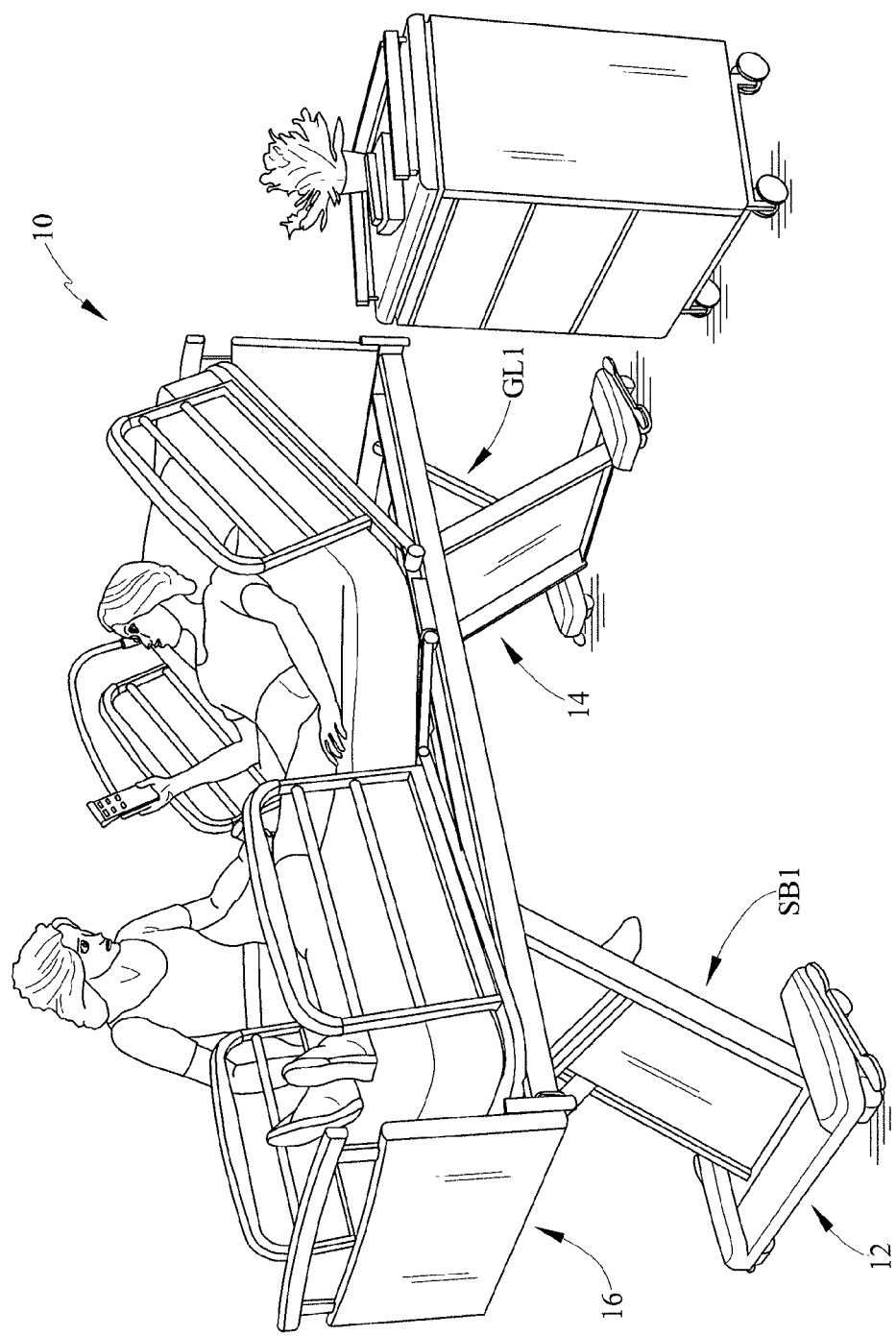
FIG. 2 is the person support apparatus of FIG. 1 with the upper frame in a raised position.

The person support apparatus 10 includes a lower frame 12 or base 12, a plurality of supports 14 coupled to the lower frame 12 and an upper frame 16 movably supported by the plurality of supports 14 above the lower frame 12 as shown in FIG. 2. In one illustrative embodiment, the supports 14 are lift mechanisms 14 that move the upper frame 16 with respect to the lower frame 12. In another illustrative embodiment, the lift mechanisms 14 cooperate with the lower frame to raise and lower the upper frame. In some contemplated embodiments, the supports 14 employ a Evans-link system where the support beam SB1 is pivotably coupled to the lower frame 12 and slidably coupled to the upper frame 16, a guide link GL1 is pivotably coupled to the upper frame 16 and the support beam SB1, and a linear actuator (not shown) engages the support beam SB1 to raise/lower the person support apparatus 10.

Figure 3:
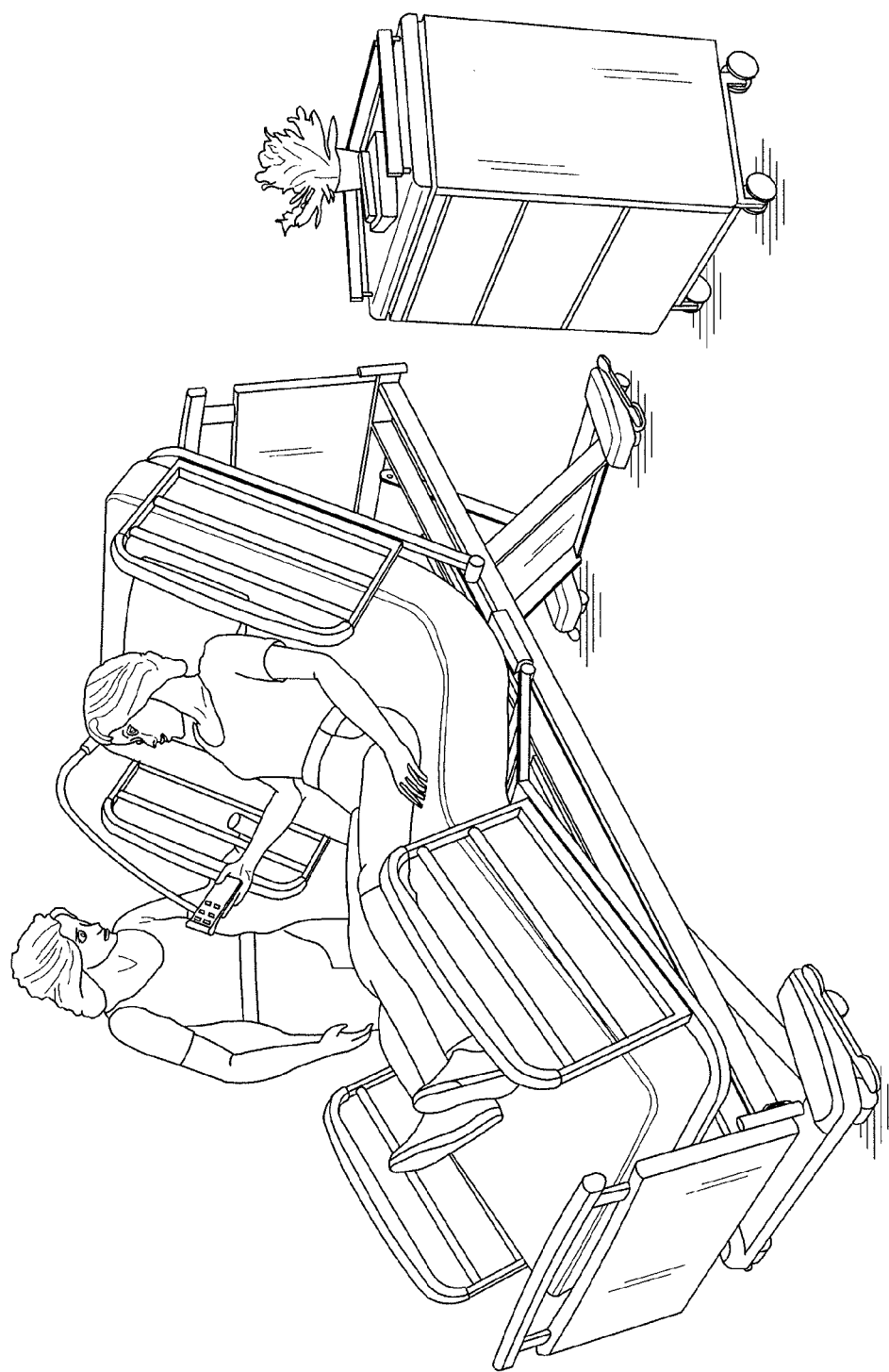
FIG. 3 is the person support apparatus of FIG. 1 in the reclined, reverse-Trendelenburg position.
Figure 4:
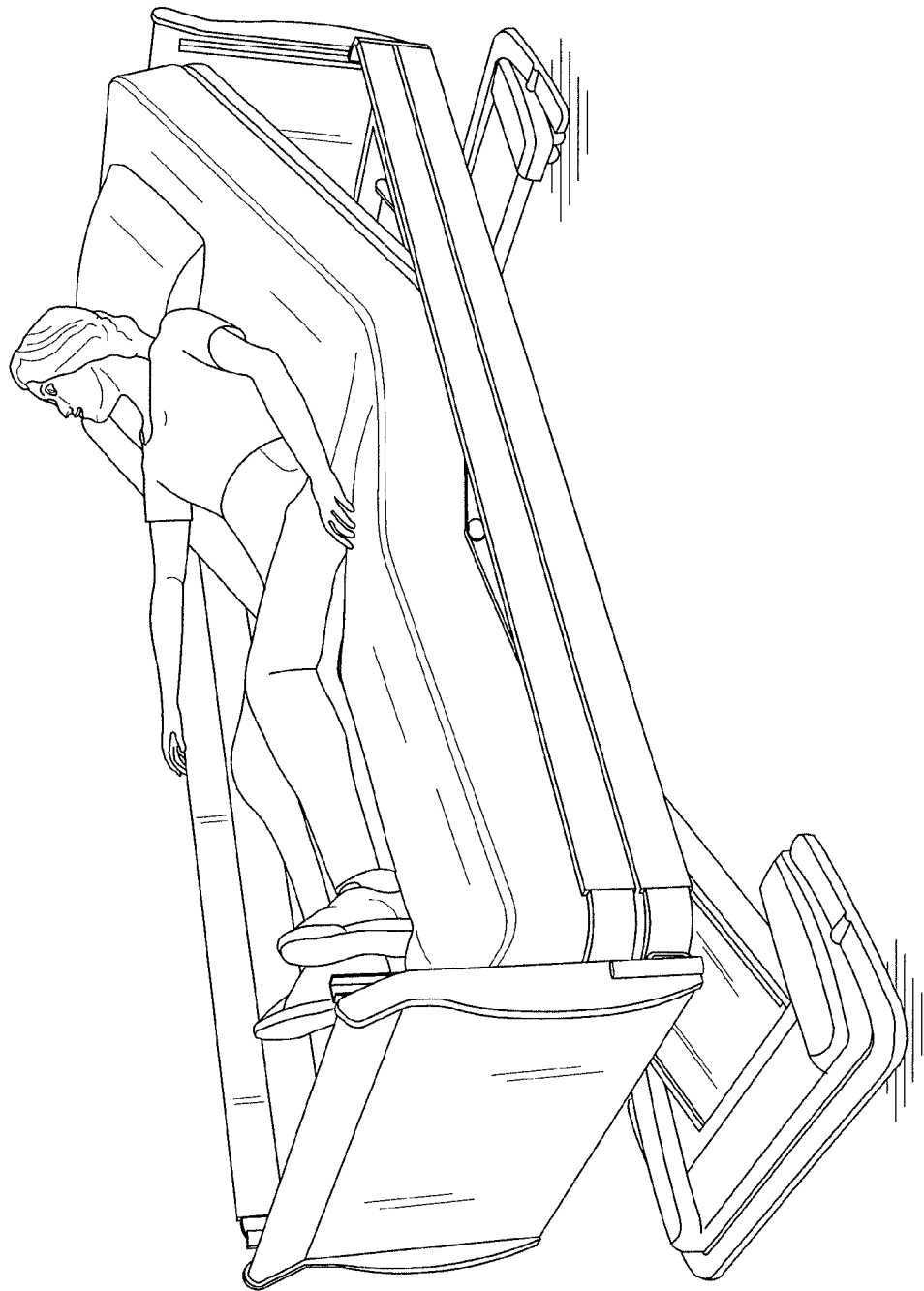
FIG. 4 is a person support apparatus according to another contemplated embodiment of the current disclosure showing a full length siderail coupled to the upper frame.
Figure 30:
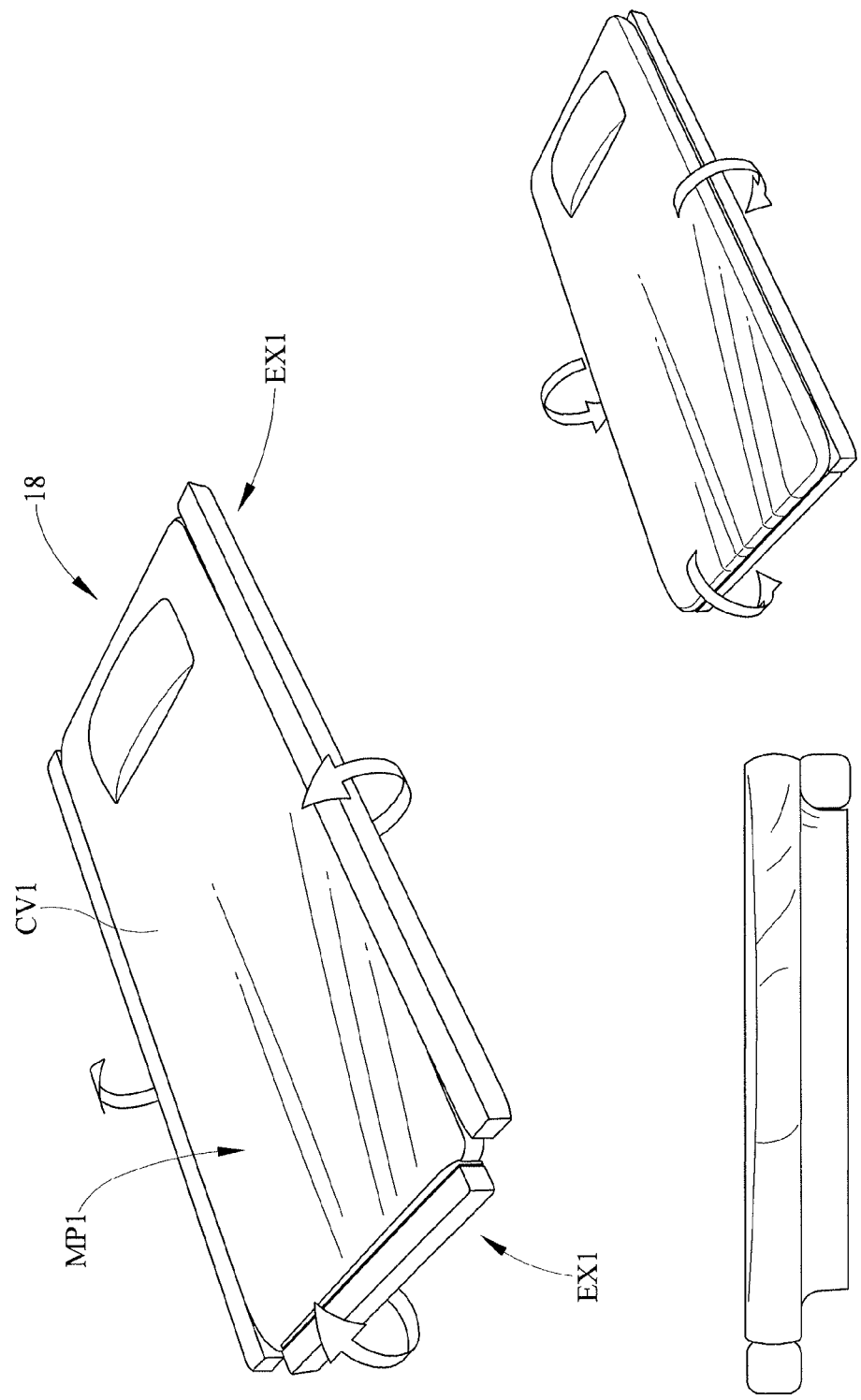
FIG. 30 is the mattress of FIG. 29 showing a main portion with extensions pivotably coupled there to that are configured to move between a nested position and an extended position.
Figure 31:
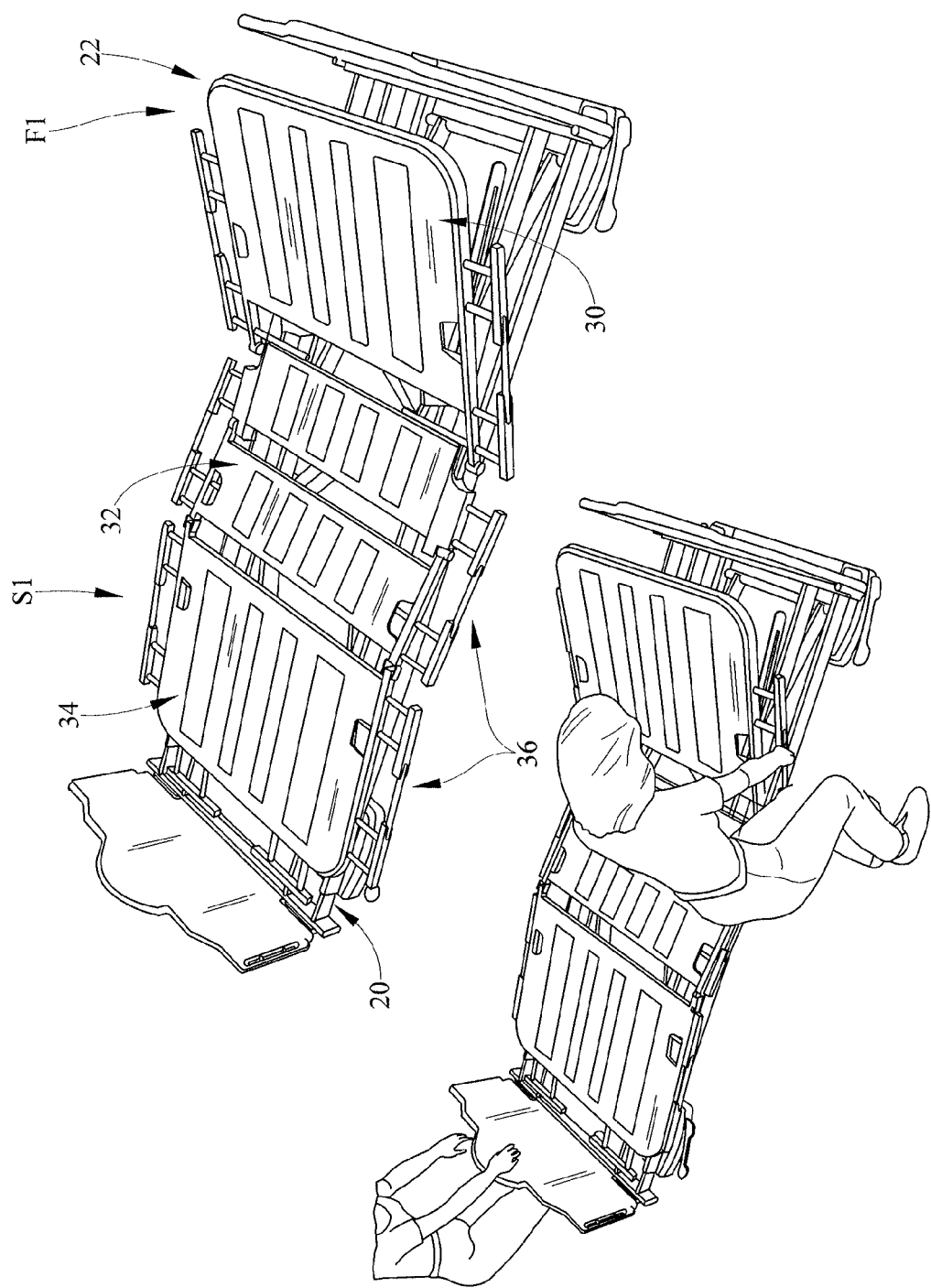
FIG. 31 is a person support apparatus according to another contemplated embodiment of the current disclosure showing the frame width and length extensions.
Figure 32:
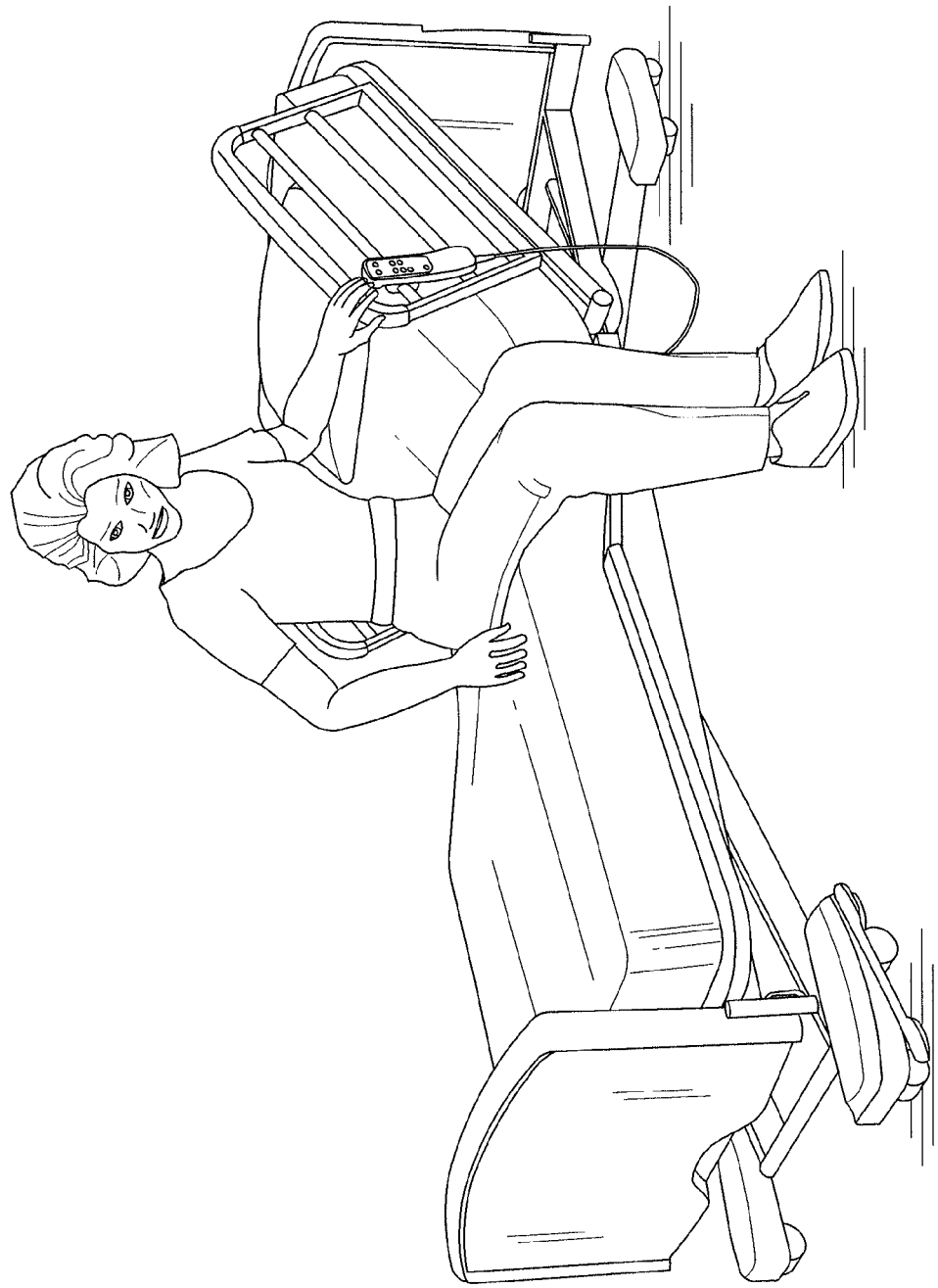
FIG. 32 is a person support apparatus according to another contemplated embodiment of the current disclosure.
Figure 33:
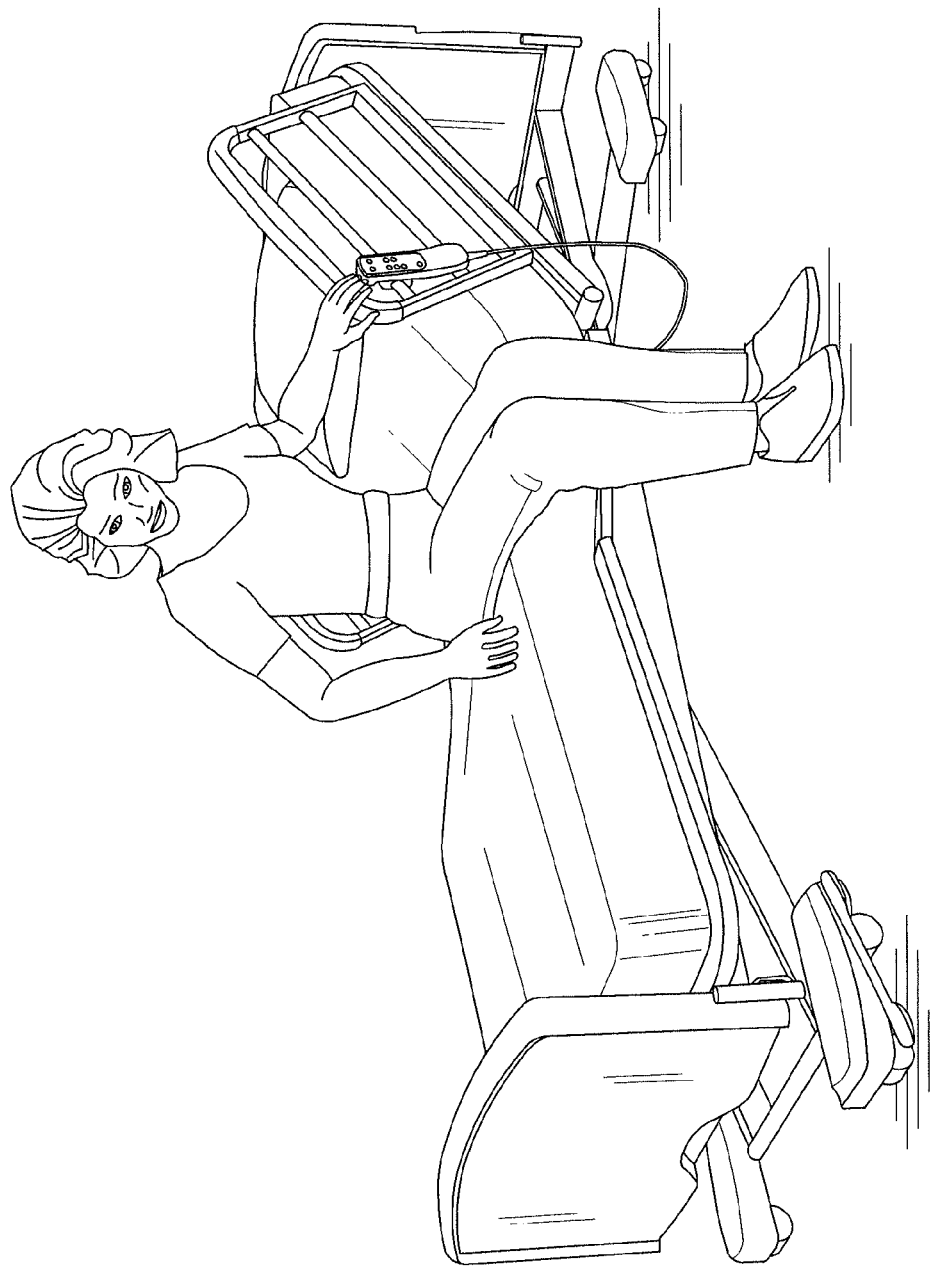
FIG. 33 is a person support apparatus according to another contemplated embodiment of the current disclosure.
Figure 34:
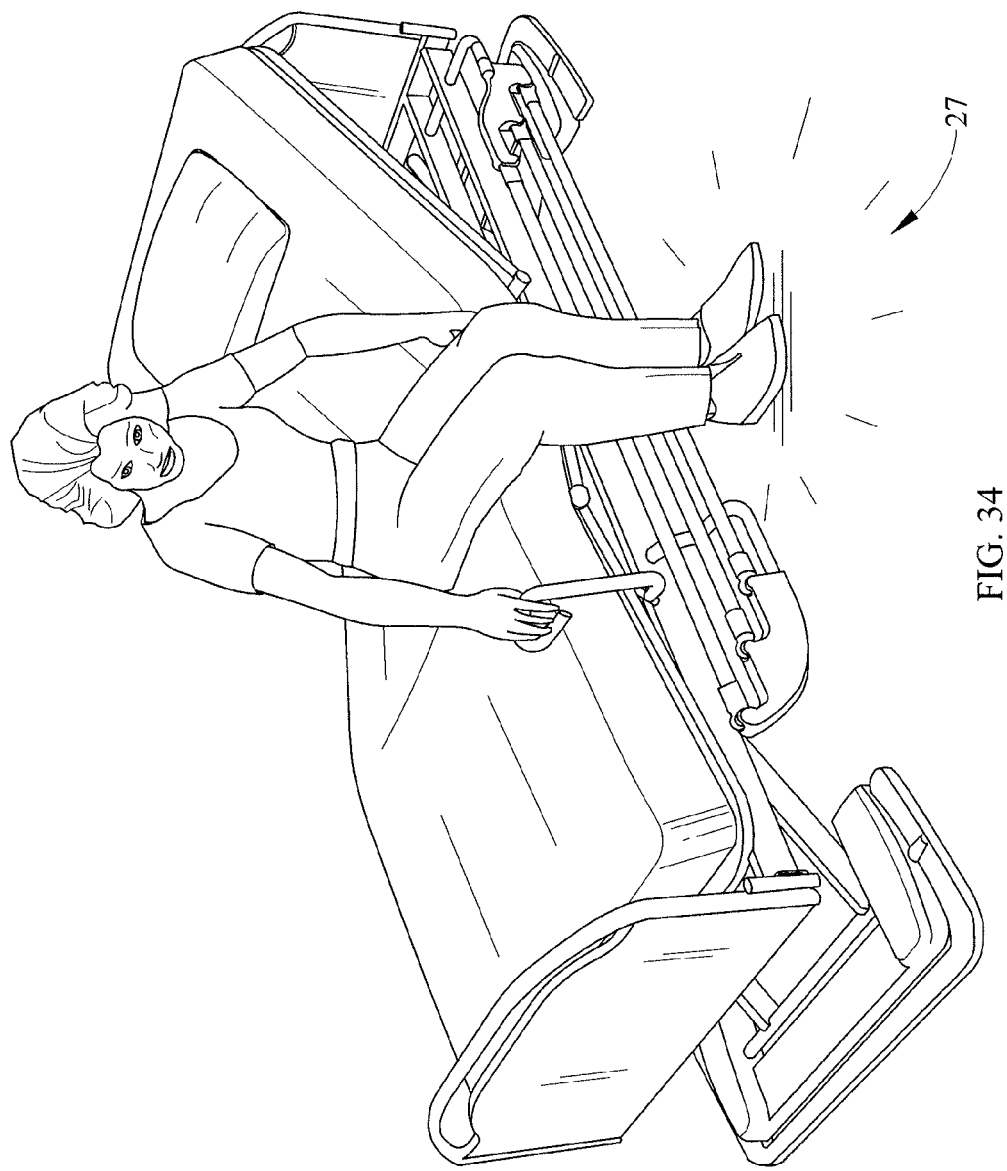
FIG. 34 is a person support apparatus according to another contemplated embodiment of the current disclosure showing a night-light configured to alert the user to a status of the person support apparatus, such as, when the person support apparatus is in a position where the occupant can egress from the bed. The light illuminating the floor with a red light to indicate that the user of an unsatisfactory condition, such as, that the bed is not in a predetermined egress position.
Figure 35:
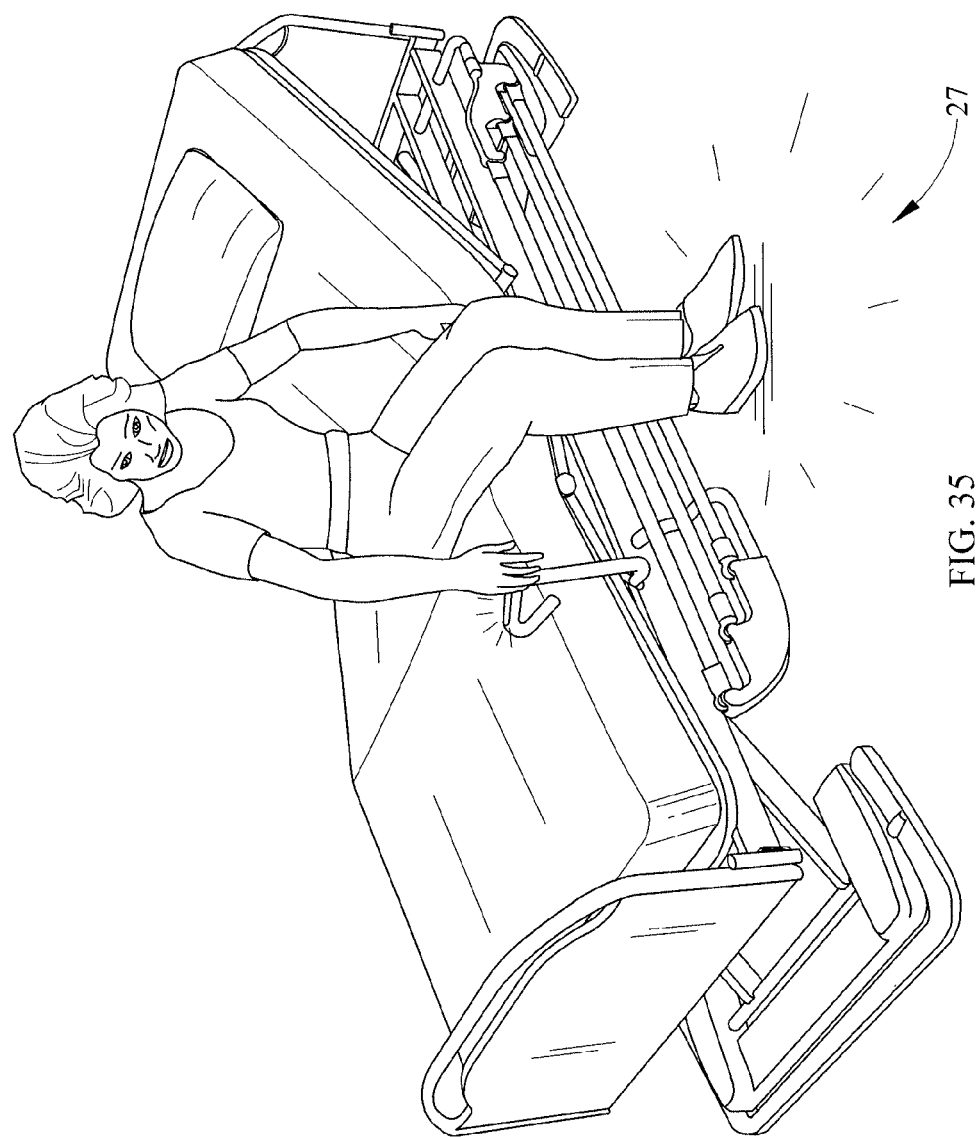
FIG. 35 is the person support apparatus of FIG. 34, wherein the handle of the grip and the floor are illuminated with a green light to indicate that the occupant can egress from the bed.

The upper frame 16 includes an upper frame base 20, a deck 22, siderails 24, endboards 26 (including a head endboard 26a and a foot endboard 26b), a control system CS1, a night light 27, and a pendant 28 as shown in FIGS. 1-47. The upper frame base 20 is coupled to the supports 14 and supports the deck 22, the siderails 24, and the endboards 26. The deck 22 includes a head portion 30, a seat portion 32, and a foot portion 34 as shown in FIGS. 1-2. The head portion 30, the seat portion 32, and the foot portion 34 are movably coupled to each other and the upper frame base 20 and are configured to cooperate with one another to move the deck 22 between a relatively horizontal position and a chair position as shown in FIG. 3. In other contemplated embodiments, the deck 22 is configured to move between a relatively horizontal position and a reclined position. The deck 22 includes deck extensions 36 that are configured to slide out from the sides of the portions of the deck 22 to increase the width of the deck 22 as shown in FIG. 31.

Figure 5:
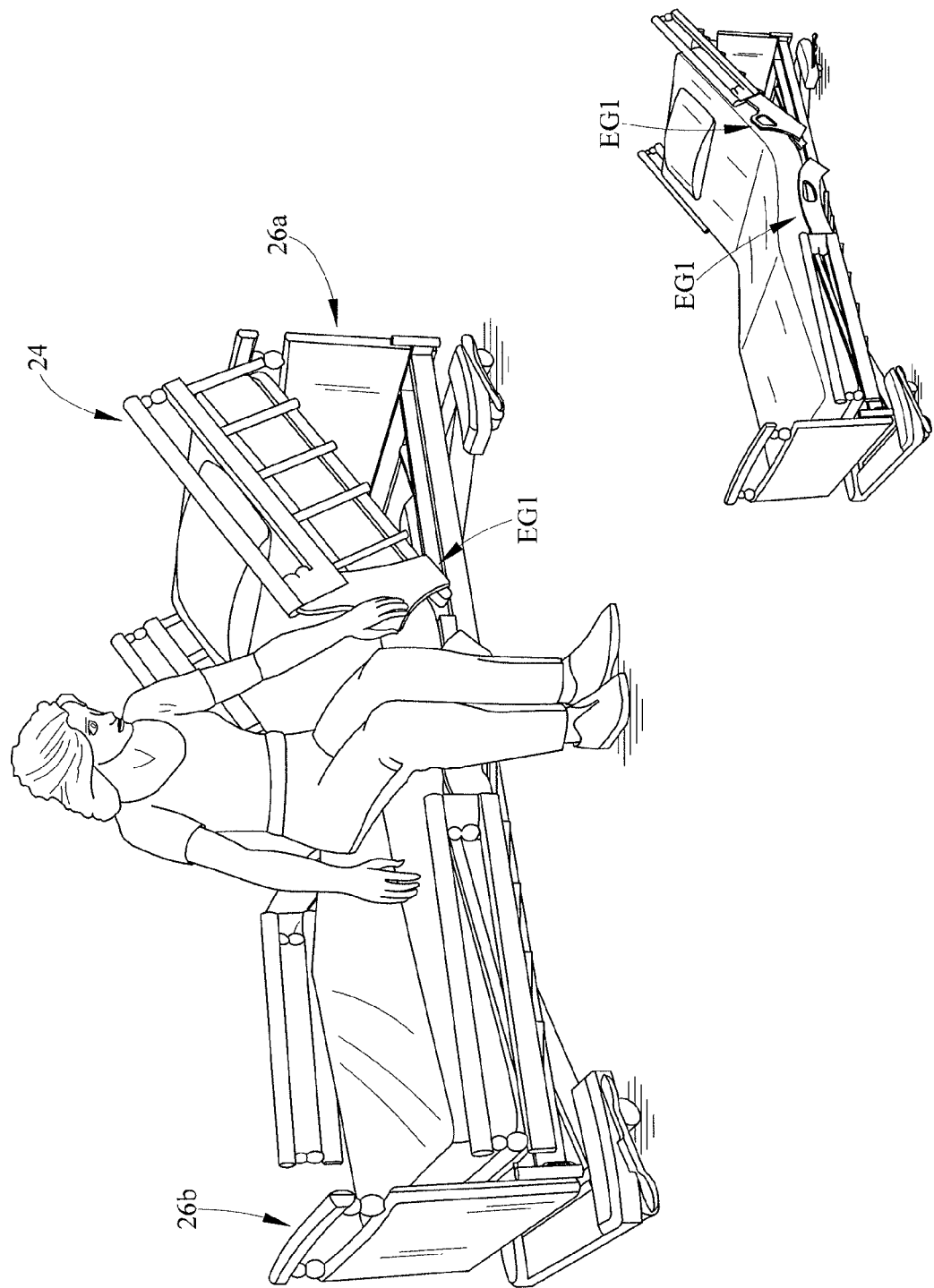
FIG. 5 is a person support apparatus according to another contemplated embodiment of the current disclosure showing a collapsible siderail with an egress grip integrated into the siderail movement mechanism.
Figure 6:
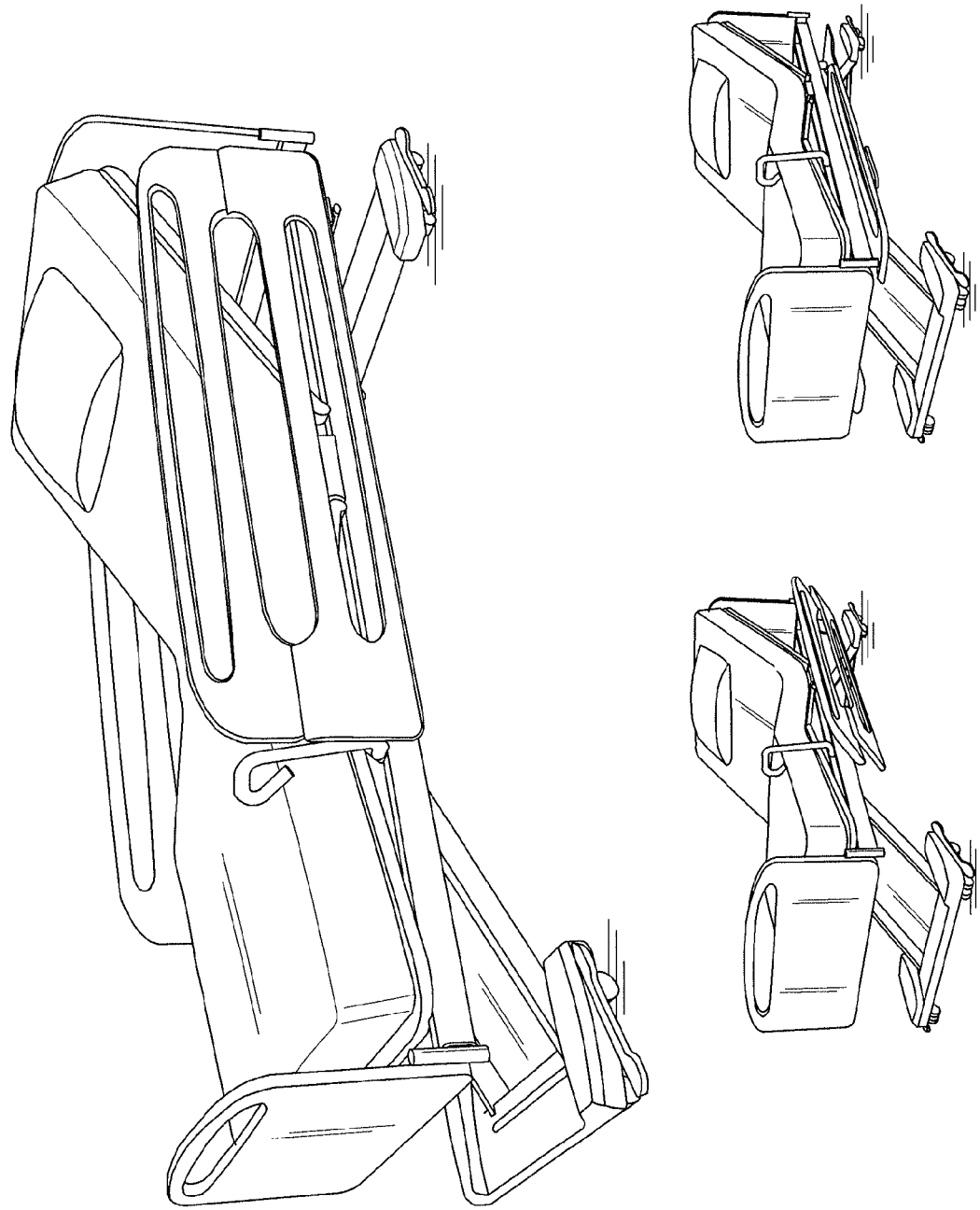
FIG. 6 is a person support apparatus according to another contemplated embodiment of the current disclosure showing an egress grip coupled to the upper frame and a foldable siderail configured to be rotated and stowed beneath the upper frame.
Figure 7:
FIG. 7 is a person support apparatus according to another contemplated embodiment of the current disclosure showing the egress grip of FIG. 6 and a collapsible, clocking siderail coupled to the upper frame.
Figure 8:
FIG. 8 is a person support apparatus according to another contemplated embodiment of the current disclosure.
Figure 9:
FIG. 9 is the person support apparatus of FIG. 8 with the foot end siderails removed.
Figure 10:
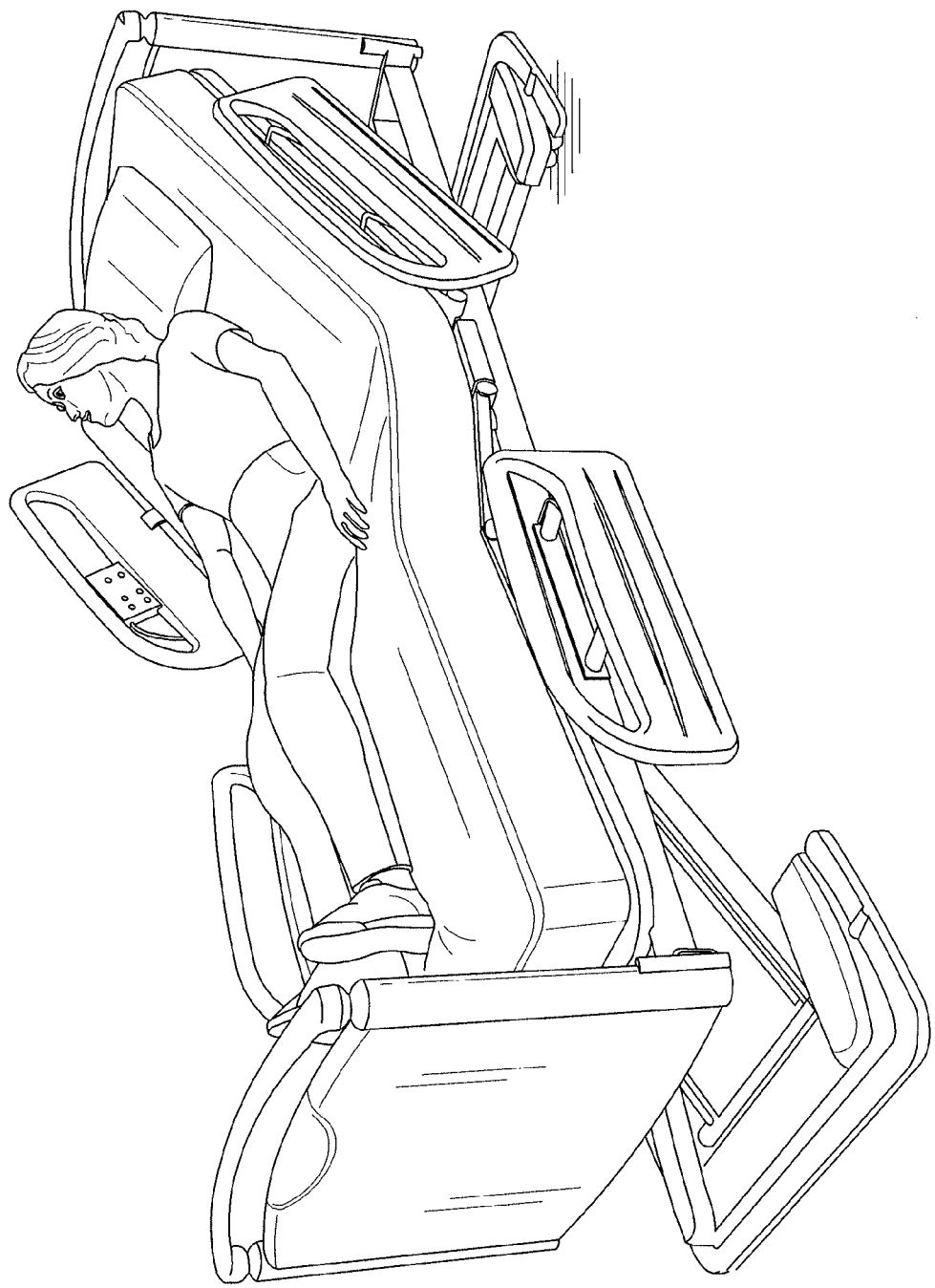
FIG. 10 is a person support apparatus according to another contemplated embodiment of the current disclosure.
Figure 11:
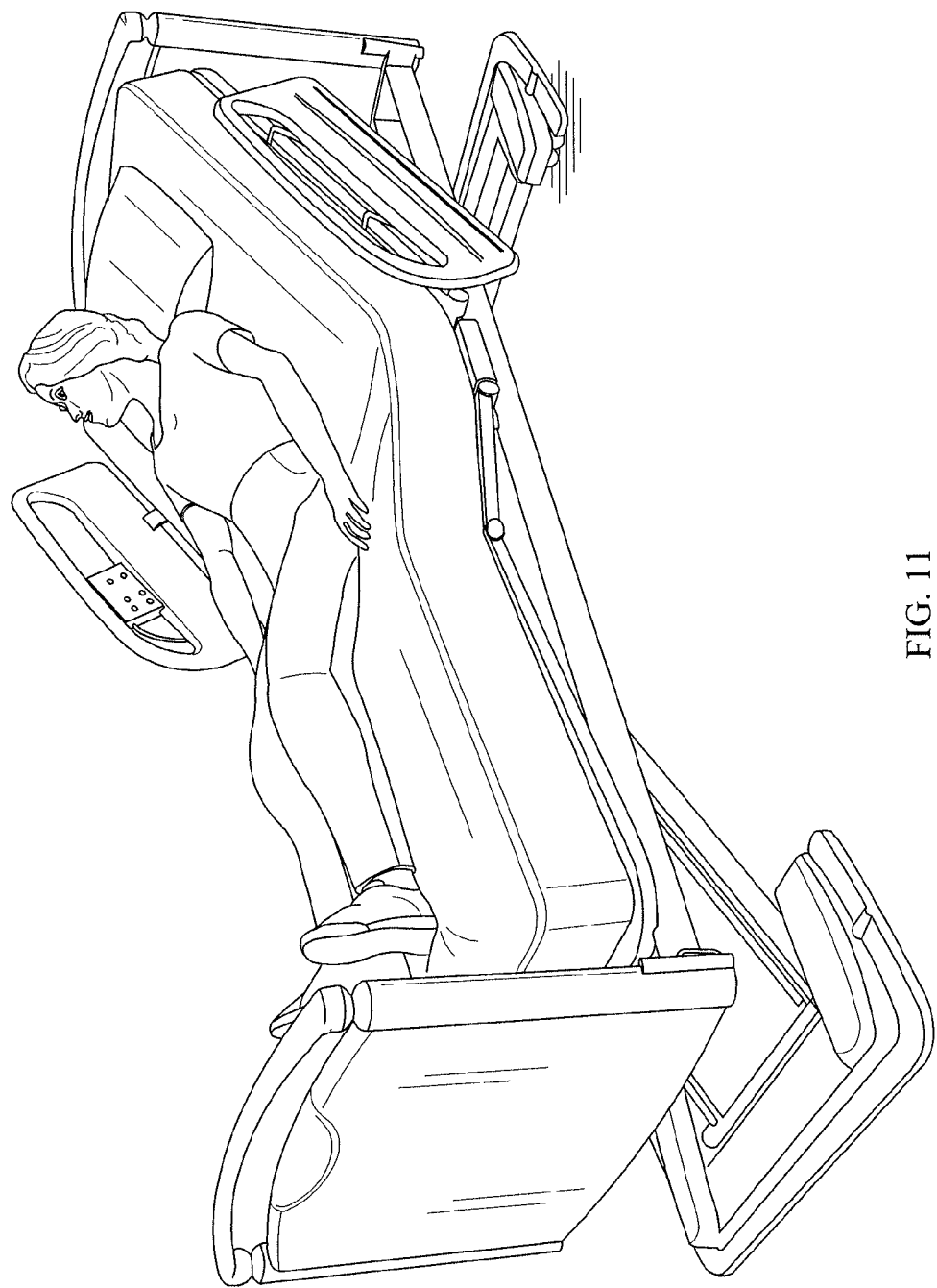
FIG. 11 is the person support apparatus of FIG. 9 with the foot end siderails removed.
Figure 12:
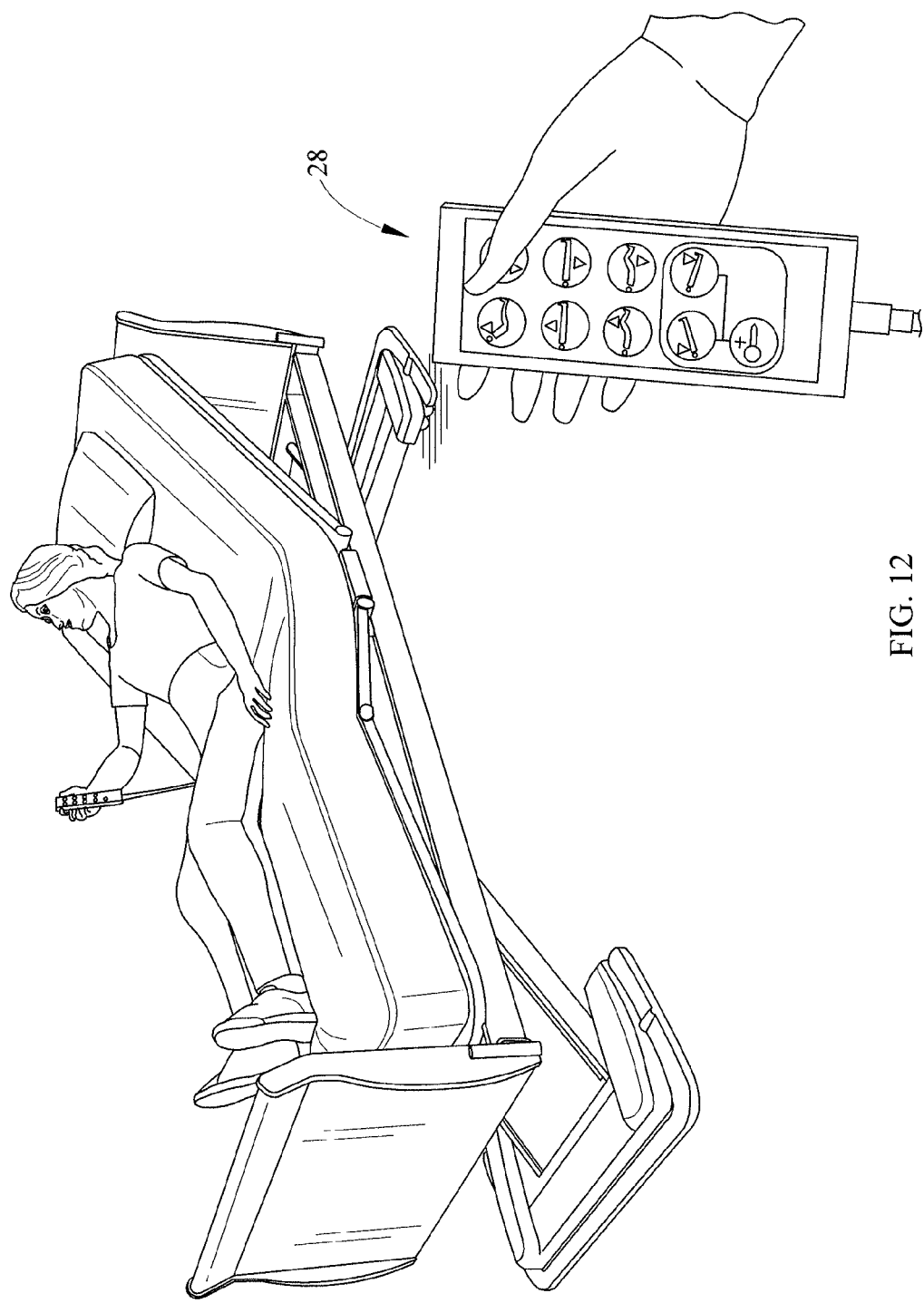
FIG. 12 is a person support apparatus according to another contemplated embodiment of the current disclosure showing a pendant and brake-steer pedals coupled to the lower frame.
Figure 13:
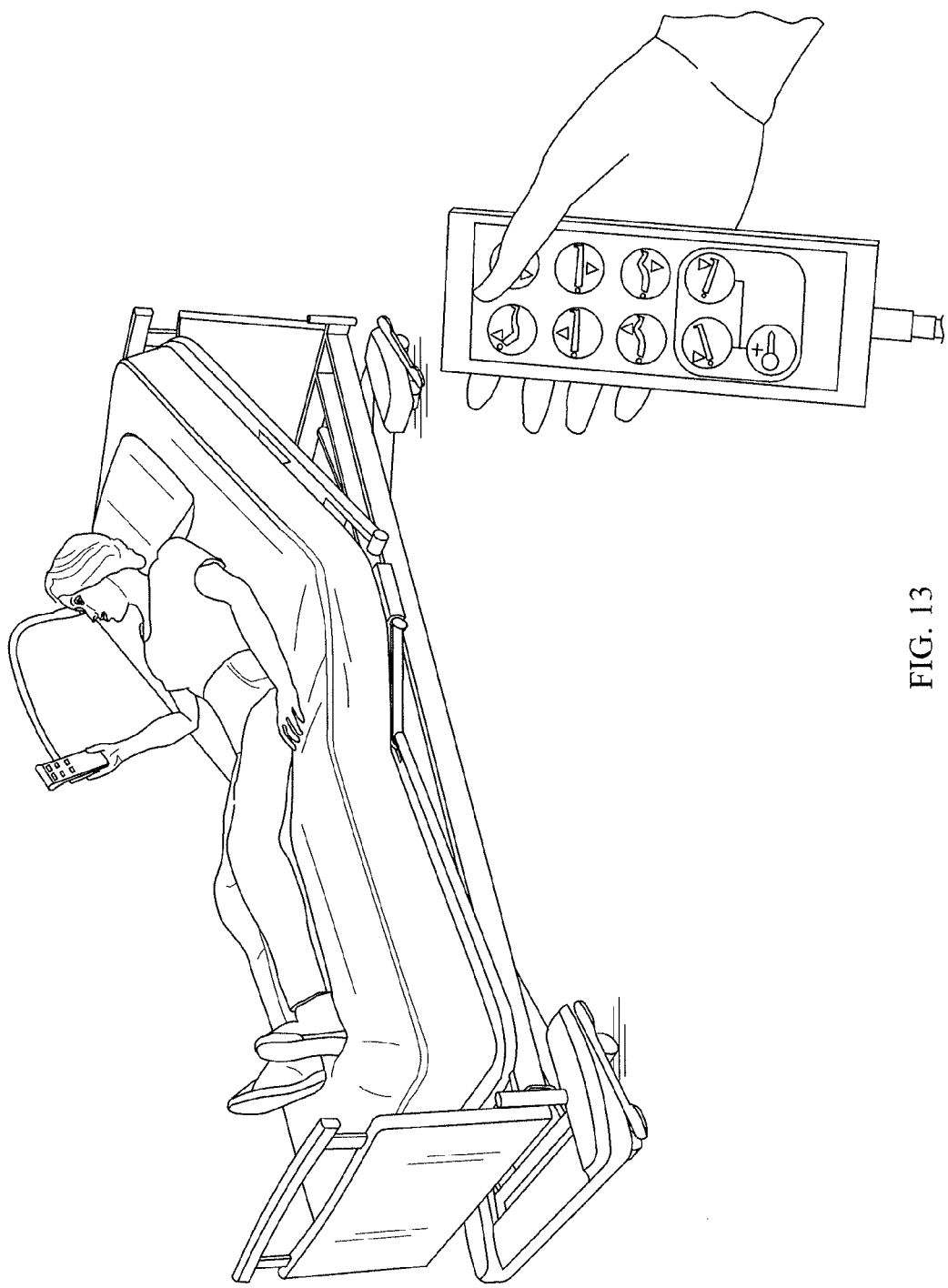
FIG. 13 is a person support apparatus according to another contemplated embodiment of the current disclosure showing a pendant holder coupled to the head end of the person support apparatus.
Figure 14:
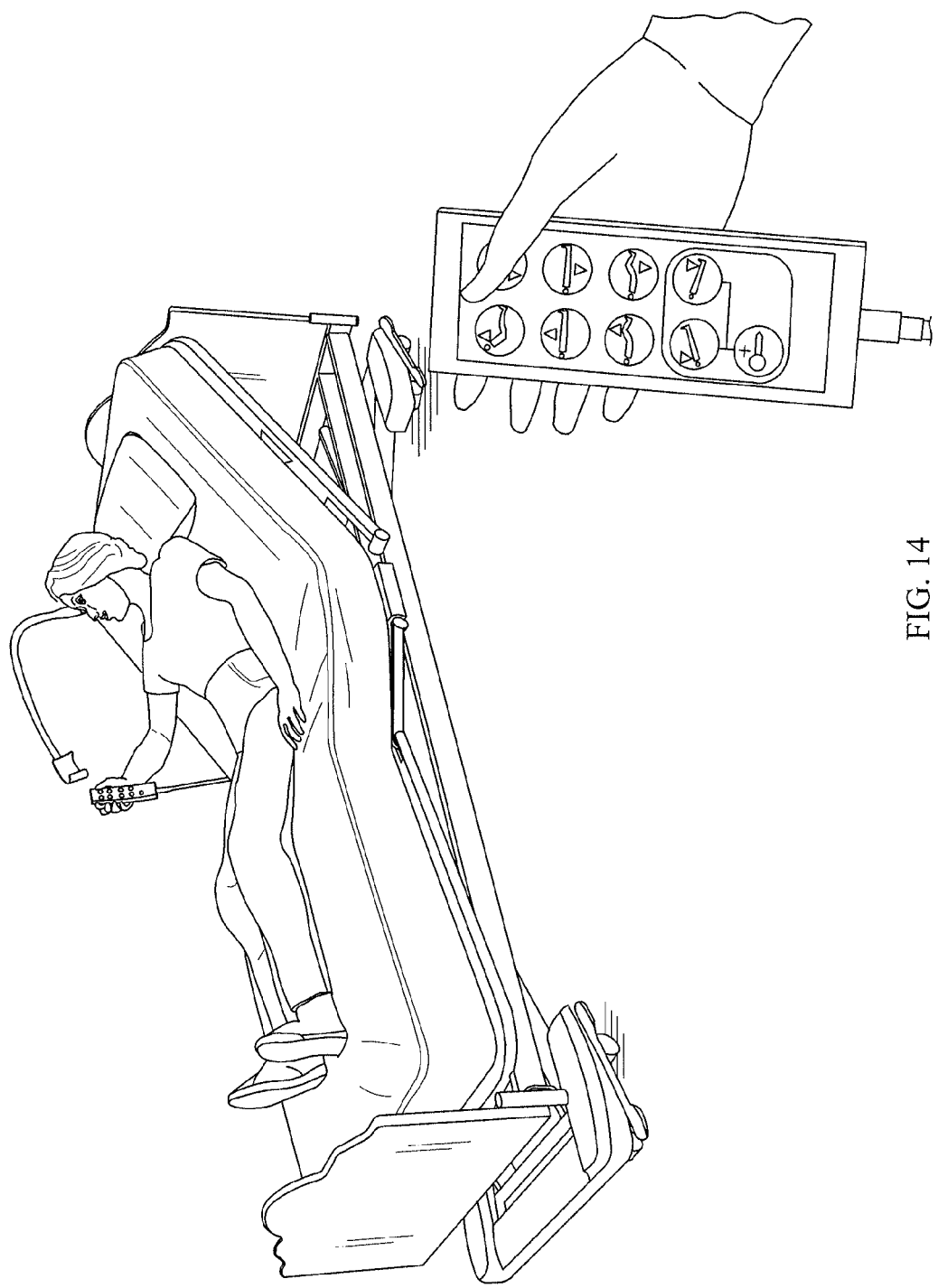
FIG. 14 is a person support apparatus of FIG. 13 according to another contemplated embodiment of the current disclosure.
Figure 15:
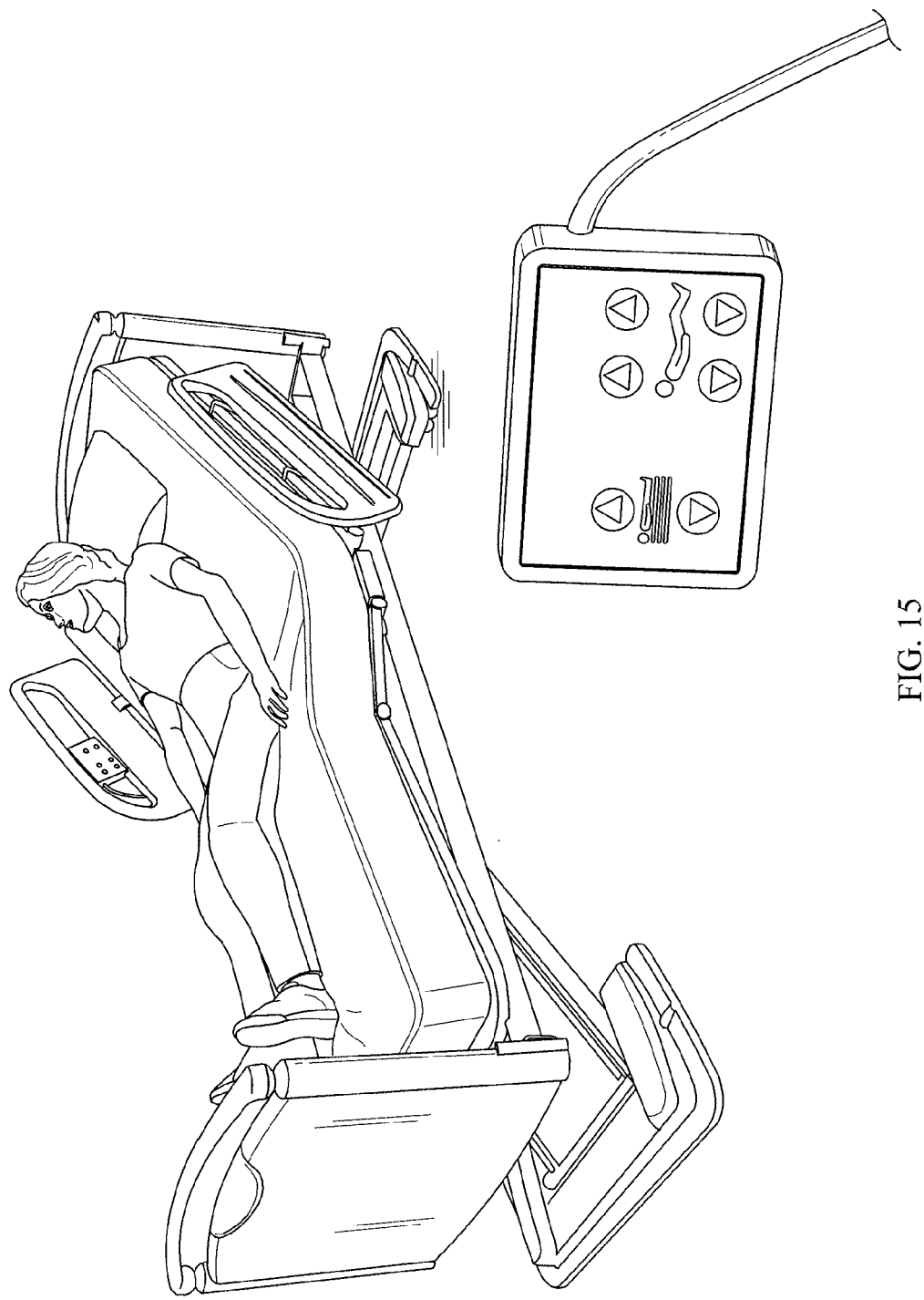
FIG. 15 is a person support apparatus according to another contemplated embodiment of the current disclosure showing a pendant coupled within the siderail grip opening of a siderail.
Figure 16:
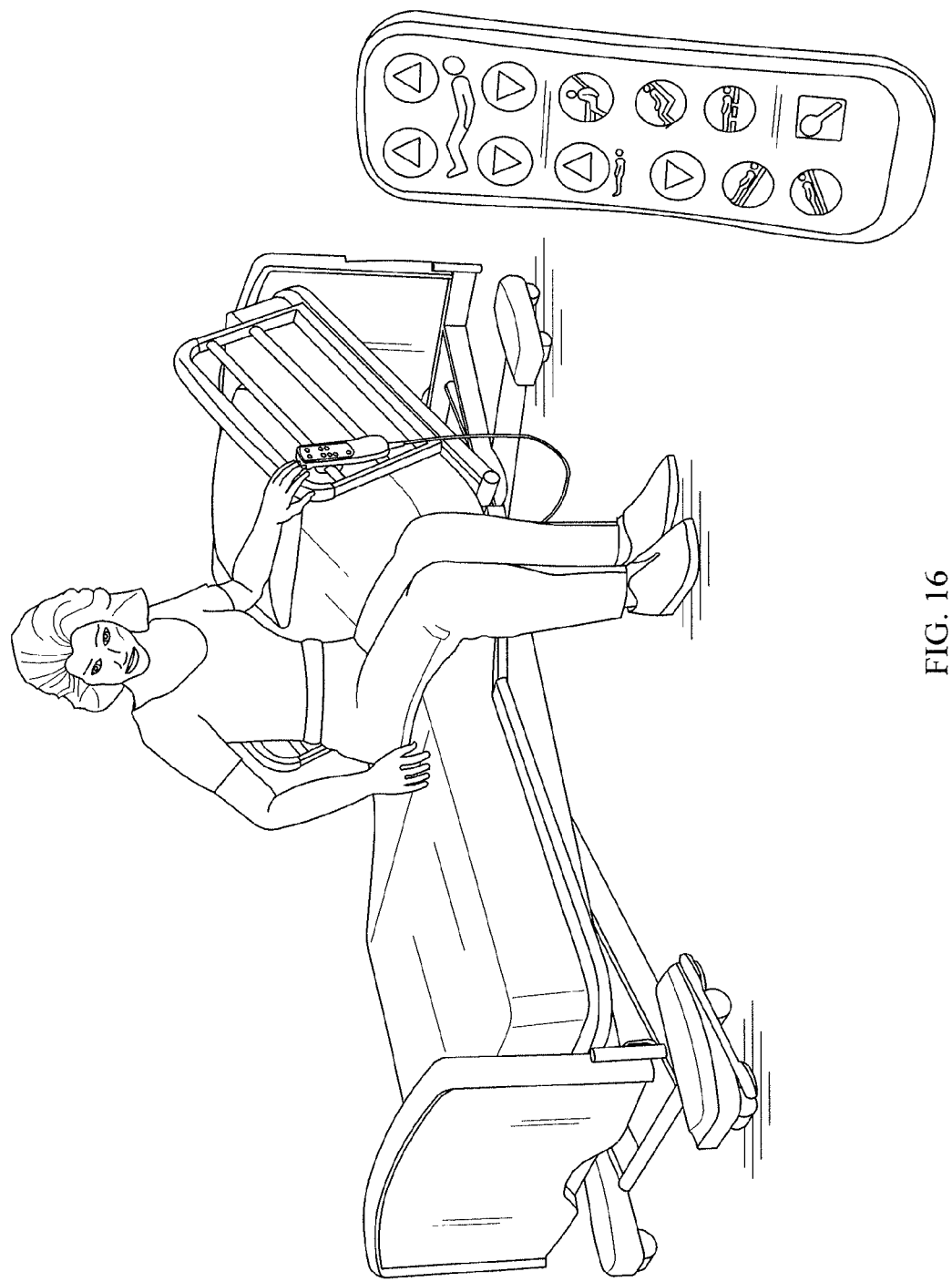
FIG. 16 is a pendant according to another illustrative embodiment of the current disclosure.

The siderails 24 include hingedly coupled to the upper frame 16 and are configured to rotate from a raised position to a collapsed storage position as shown in FIG. 5. The siderails 24 include an egress grip portion EG1 configured to provide assistance to a person egressing/ingressing to/from the person support apparatus 10. The adjacent egress grip portions shown in the figures cooperate to satisfy siderail gap requirements specified in regulation 2-52.

Figure 29:
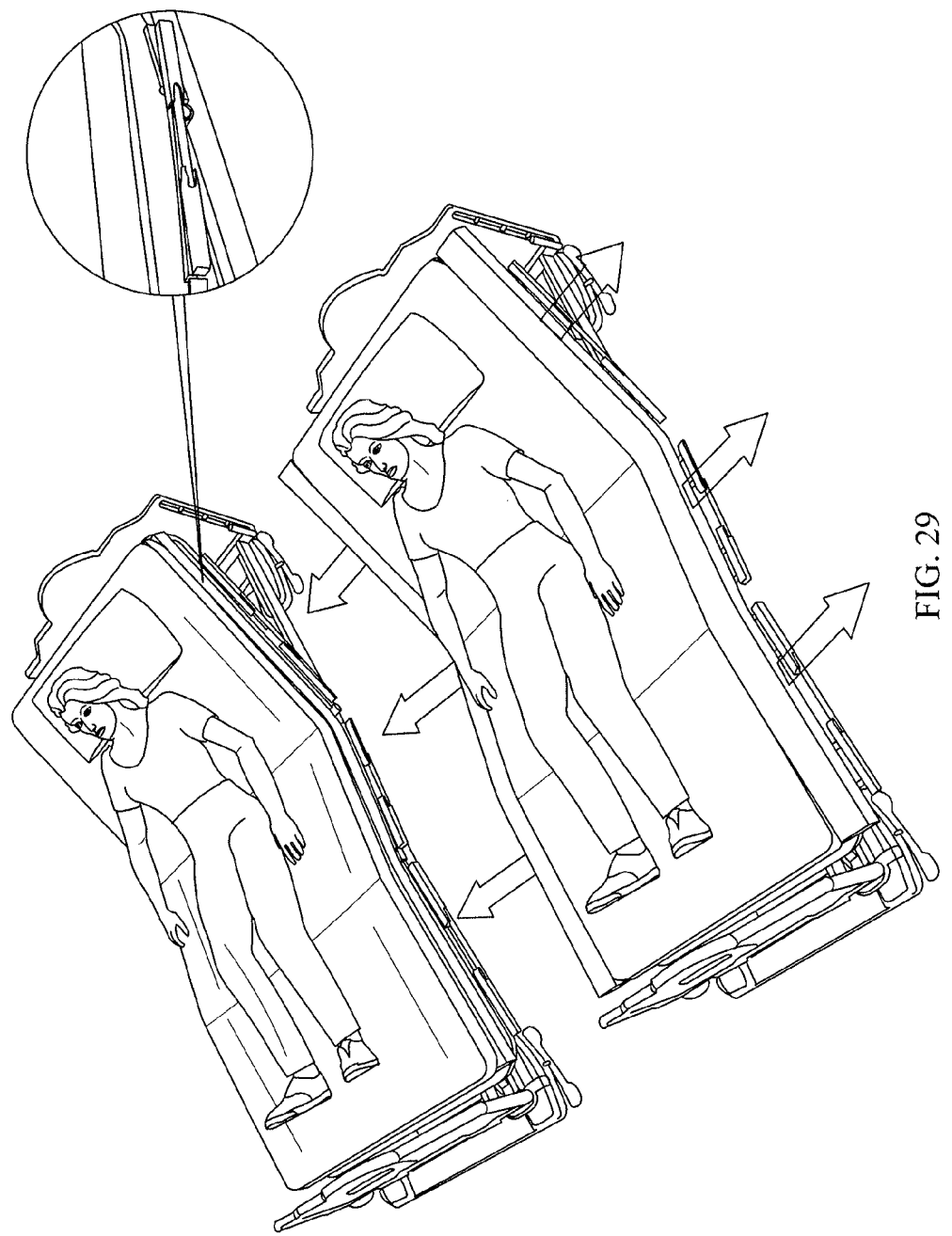
FIG. 29 is a person support apparatus according to another contemplated embodiment of the current disclosure showing a width and/or length adjustable mattress positioned thereon.

In some contemplated embodiments, the person support apparatus 10 supports a person support surface 18 or mattress 18 on the upper frame 16. The person support surface 18 includes a main mattress portion MP1 and extensions EX1 configured to extend from the sides and foot end of the main portion MP1 as shown in FIGS. 29 and 30. The extensions EX1 are coupled to the main portion MP1 via a hinge and are manually moved from a nested or retracted position where two surface of the extensions EX1 are substantially flush with the side and bottom surfaces of the main portion MP1 to an extended or deployed position where a surface of the extensions EX1 are substantially co-planar with the upper surface of the main portion MP1. In one contemplated embodiment, at least one of the extension and the main portion are composed of foam. In another contemplated embodiment, at least one of the main portion and the extension include a static gas bladder. In another contemplated embodiment, at least one of the main portion and the extension includes an air bladder. The main portion and the extension are enclosed in a cover CV1 (or ticking) including a first chamber where the main portion is positioned and a second chamber were the extension is positioned; the first chamber and the second chamber are separated by the hinge, which in some contemplated embodiments is a stitched seam. The top surface of the main portion is a first length and the bottom surface of the main portion is a second length, which is less than the first length. In one contemplated embodiment, the first length is the second length plus the width of the extension(s). The extensions EX1 are supported on the deck extensions 36 when they are in the extended position. In some contemplated embodiments, the extensions EX1 include a load bearing resin panel that is configured to span the gaps between parts of the deck extensions 36 and provide support to an occupant on the extension EX1.

Figure 36:
FIG. 36 is the person support apparatus of FIG. 34, wherein the light displays a message on the floor to indicate that the user should not exit the person support apparatus.
Figure 37:
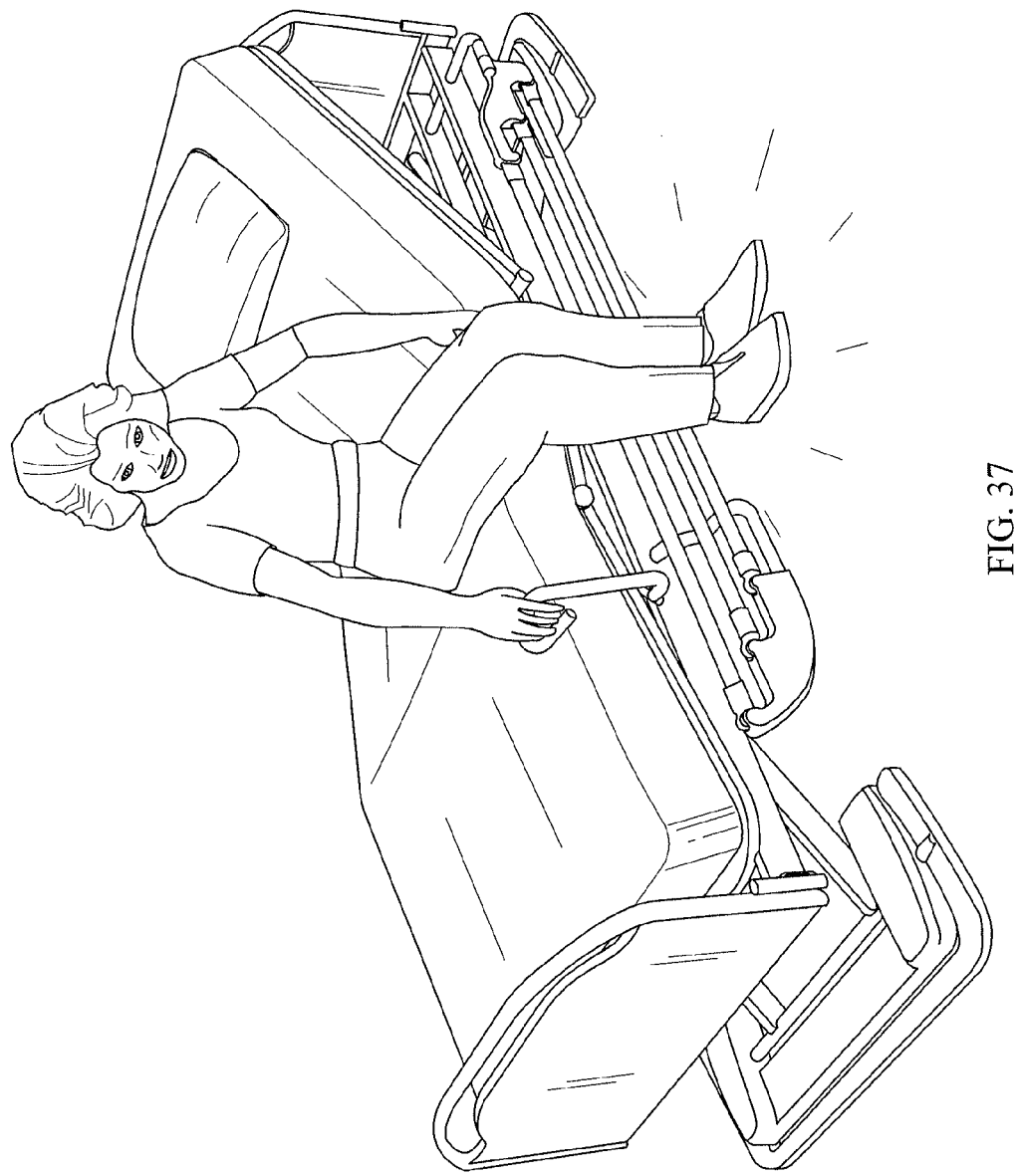
FIG. 37 is the person support apparatus of FIG. 34, wherein the light is a standard night light.
Figure 38:
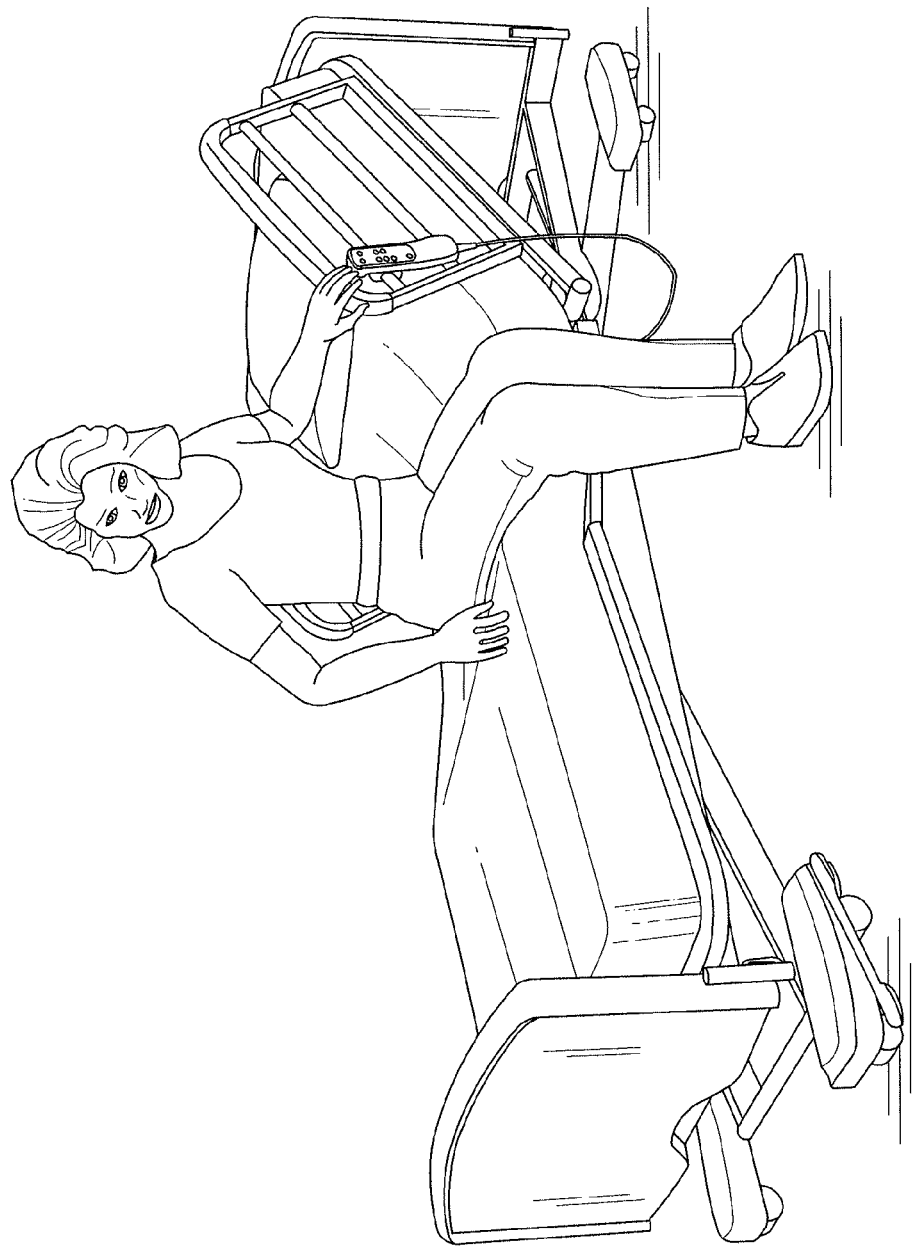
FIG. 38 is a person support apparatus according to another contemplated embodiment of the current disclosure.
Figure 39:
FIG. 39 is a person support apparatus according to another contemplated embodiment of the current disclosure.
Figure 40:
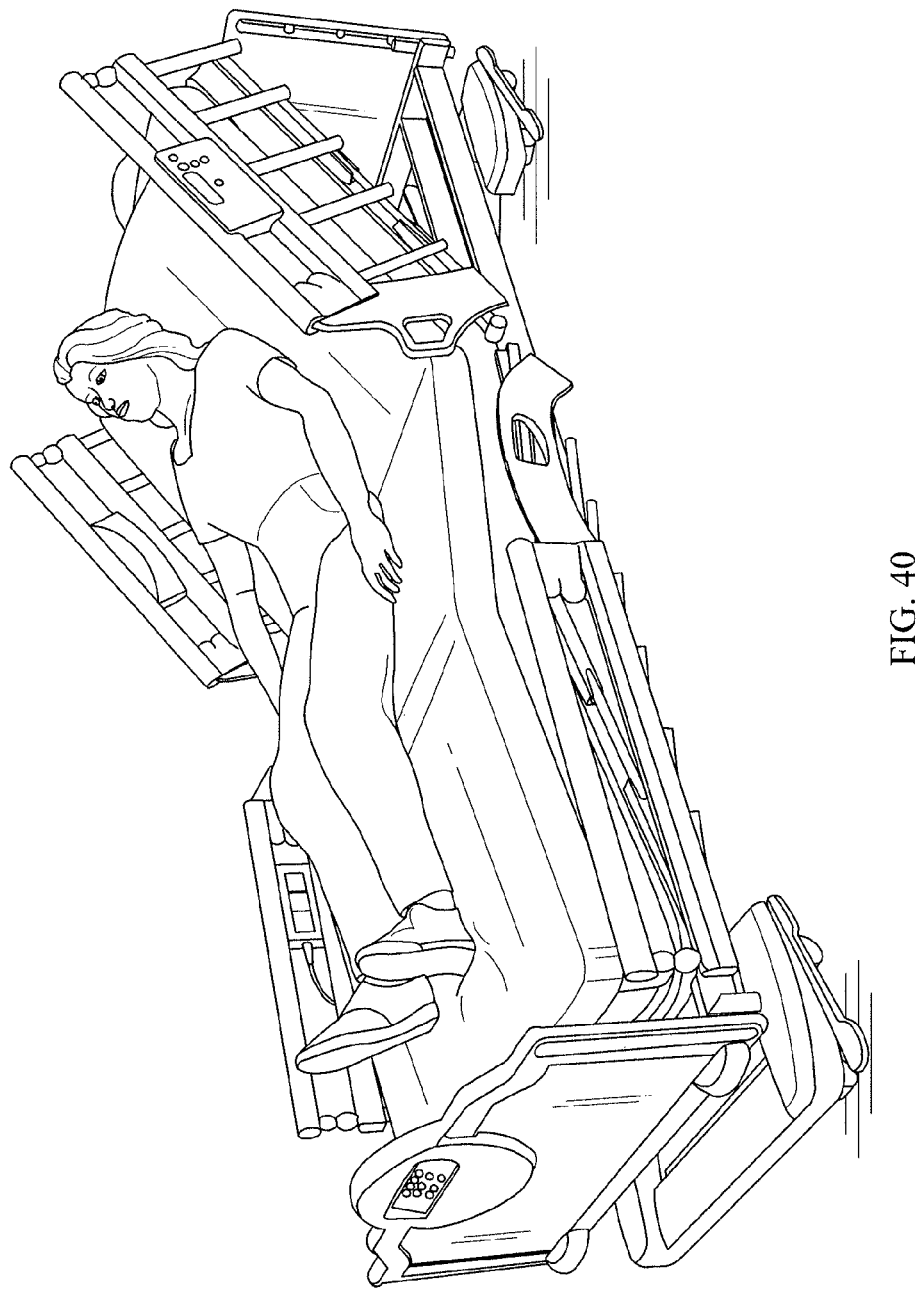
FIG. 40 is a person support apparatus according to another contemplated embodiment of the current disclosure.
Figure 42:
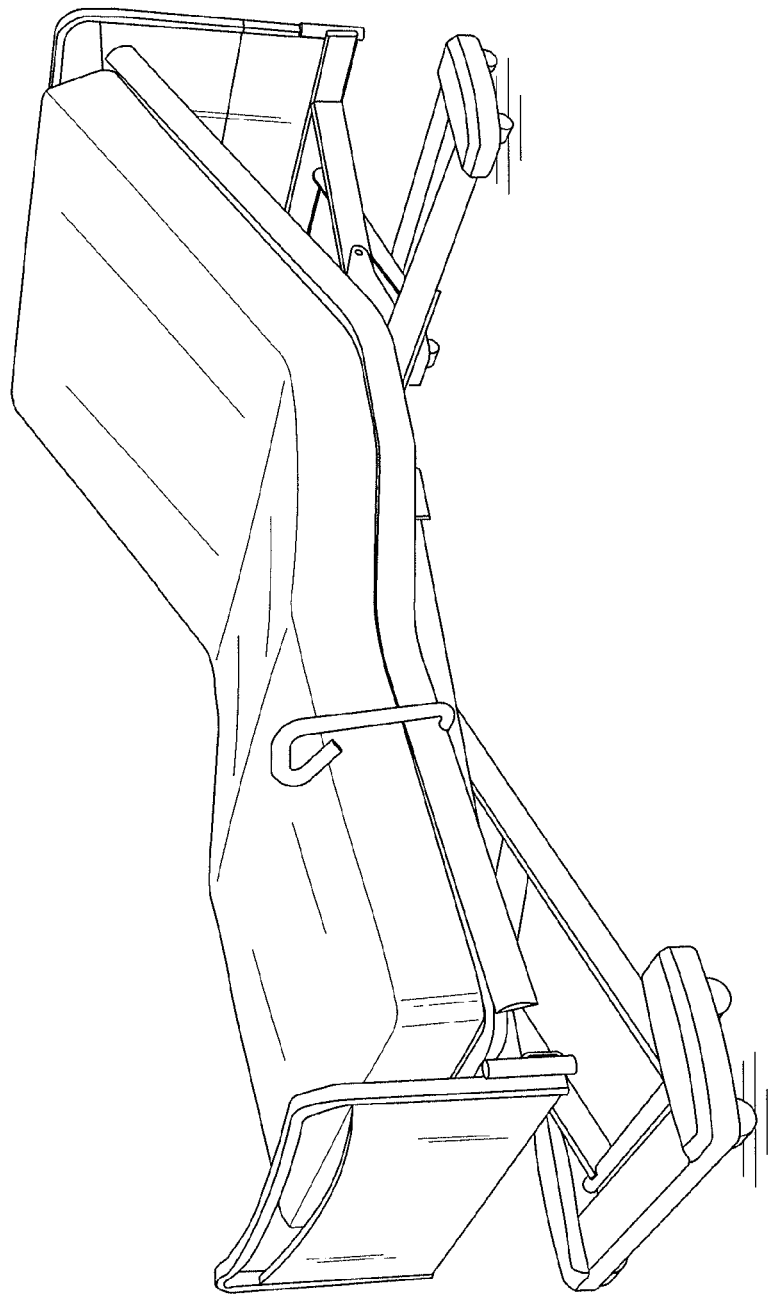
FIG. 42 is a person support apparatus according to another contemplated embodiment of the current disclosure.
Figure 43:
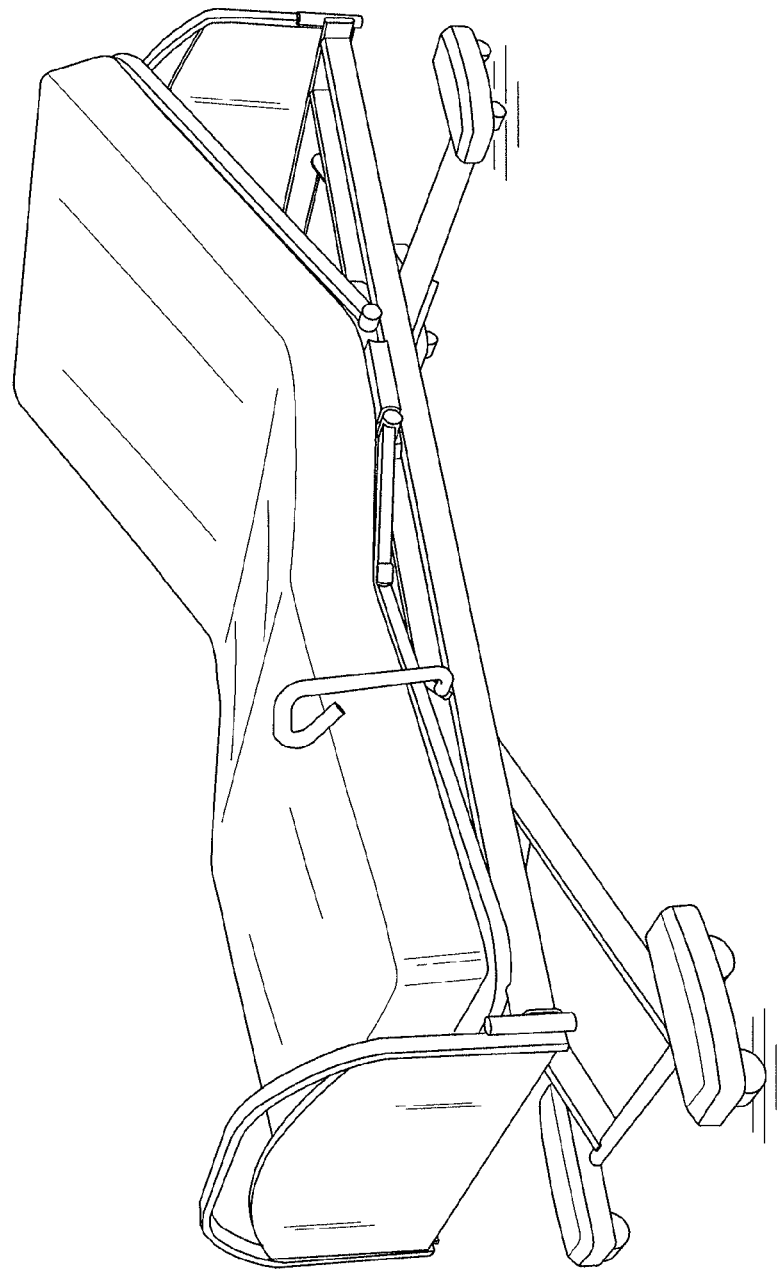
FIG. 43 is a person support apparatus according to another contemplated embodiment of the current disclosure.
Figure 44:
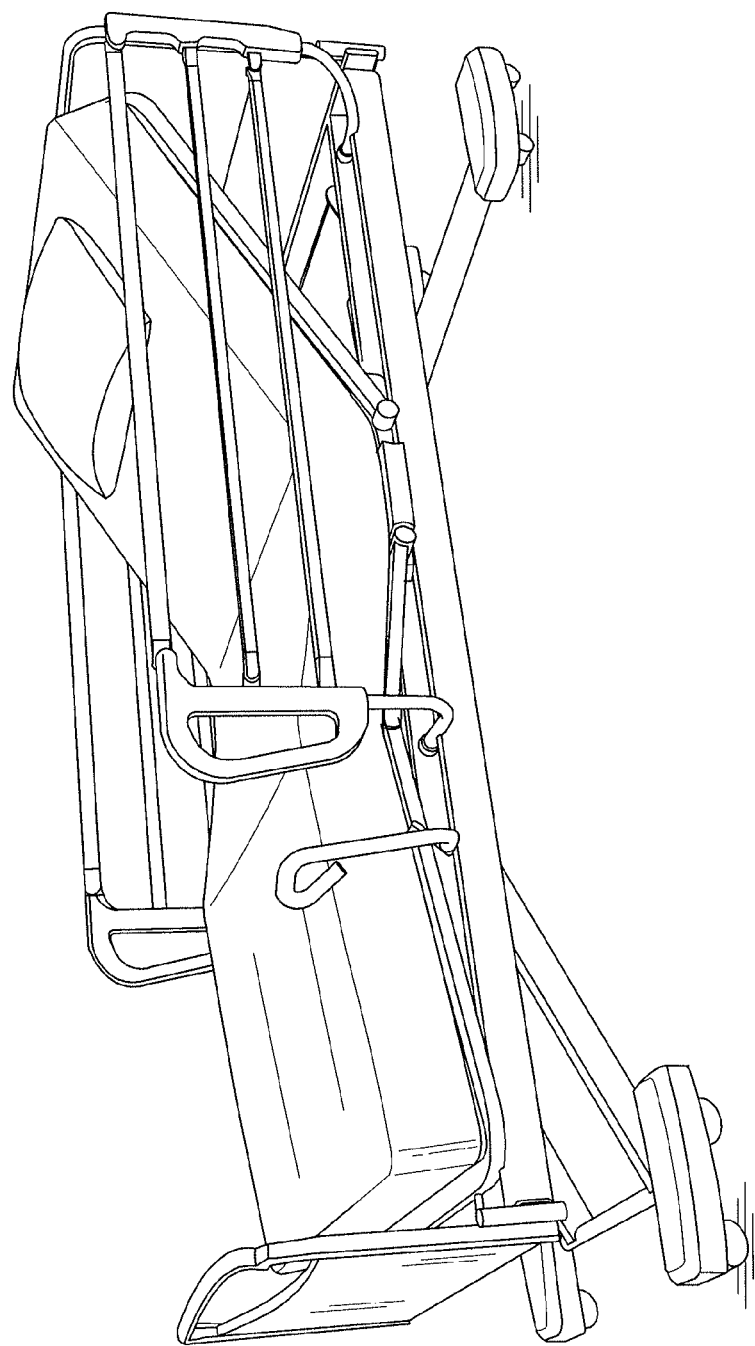
FIG. 44 is a person support apparatus according to another contemplated embodiment of the current disclosure.
Figure 45:
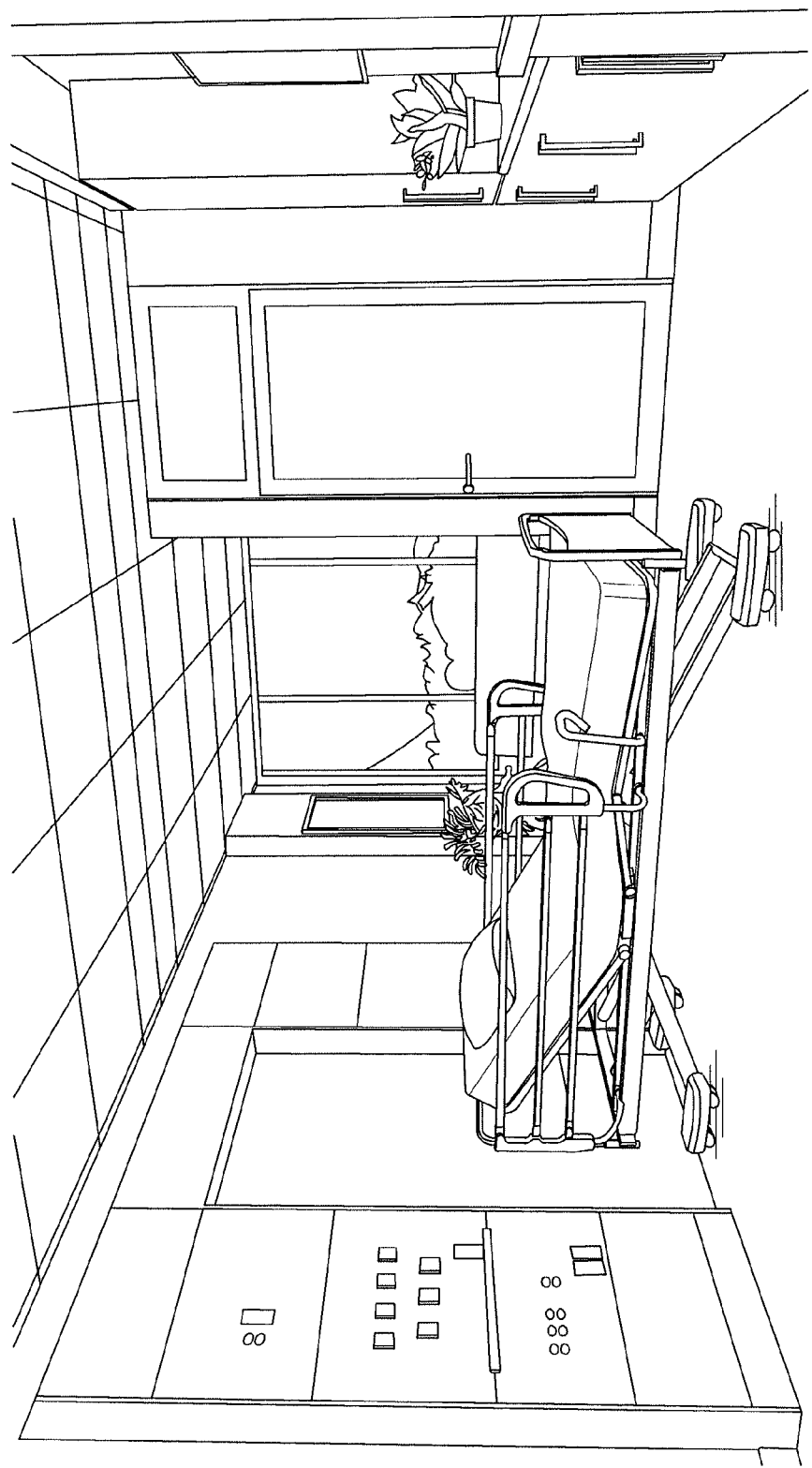
FIG. 45 is a person support apparatus according to another contemplated embodiment of the current disclosure.
Figure 46:
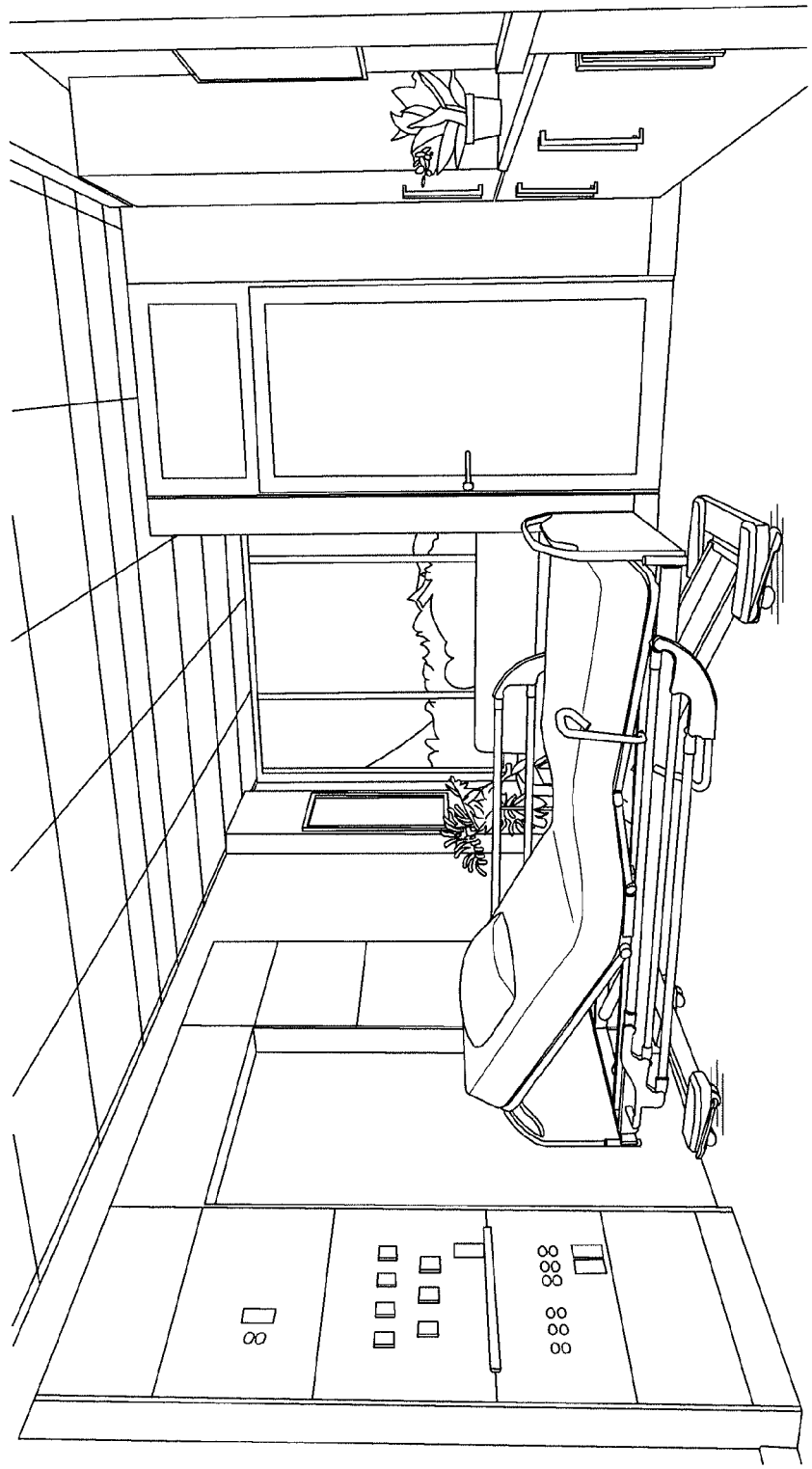
FIG. 46 is a person support apparatus according to another contemplated embodiment of the current disclosure.
Figure 47:
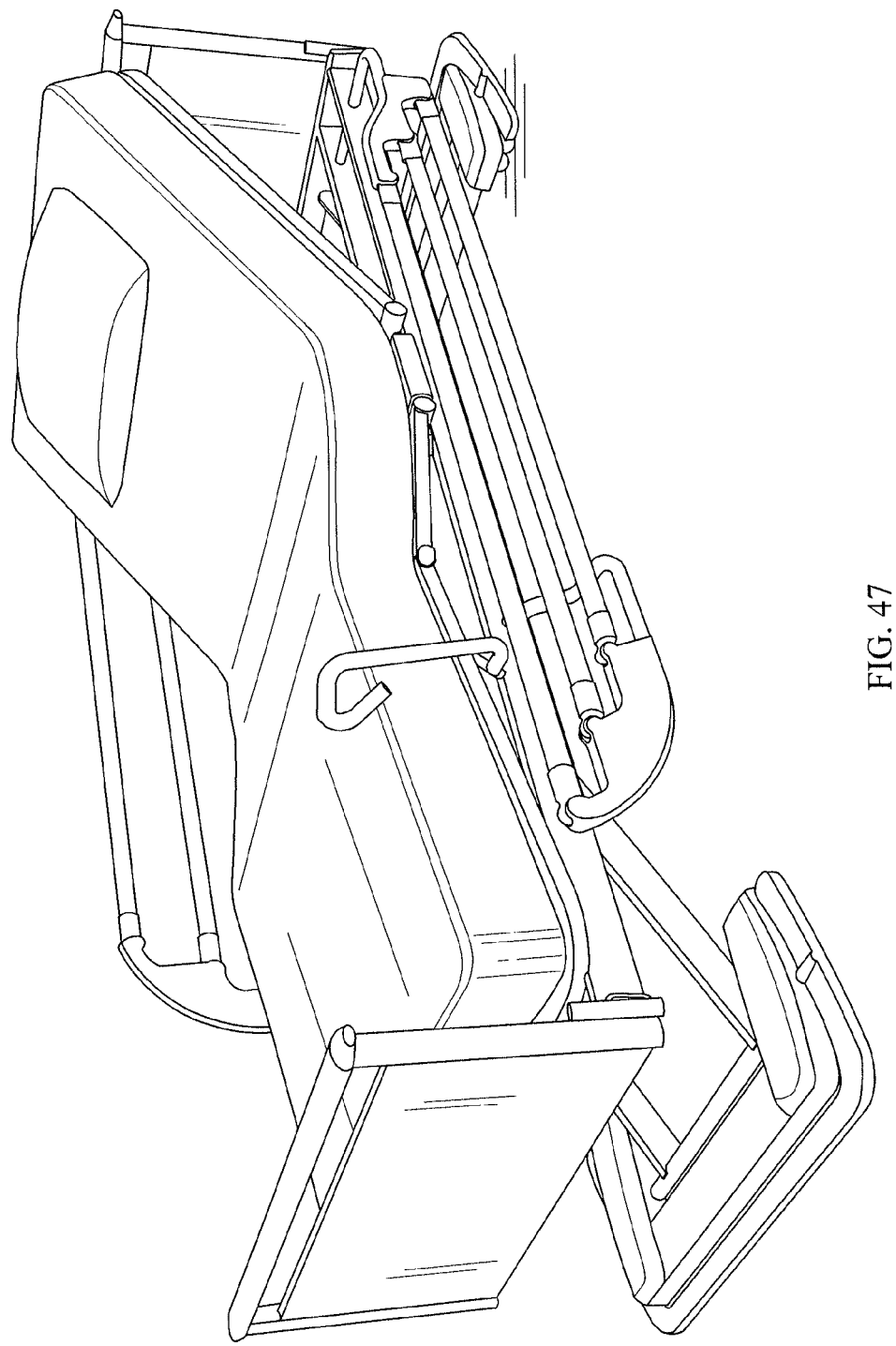
FIG. 47 is a person support apparatus according to another contemplated embodiment of the current disclosure.

The night light 27 is coupled to the upper frame 16 and is configured to shine a light on the floor when the ambient lighting is below a predetermined threshold as shown in FIGS. 33-36. In one illustrative embodiment, the night light 27 is configured to inform a person as to when the upper frame 16 is at a height where the person can egress the bed more easily. In one illustrative embodiment, the light is amber colored when the person should not exit the person support apparatus 10 and green when the person should exit the person support apparatus 10. In another illustrative embodiment, the night light 27 also displays a message on the floor to inform the occupant as to when they should egress from the person support apparatus 10. In one contemplated embodiment, the message includes words, such as, "DO NOT EXIT." In other contemplated embodiments, the message includes images, such as, a stop sign, a nurse call icon, a caution symbol (triangle with an exclamation point within the triangle). In some contemplated embodiments, the messages are displayed in multiple colors. The messages can be formed by filtering the light produced by the night light so that only the message shines through the filter. In some contemplated embodiments, the light is filtered so that the message is outlined on the floor. The filter can be implemented digitally so that certain lights in an array of lights are activated, or by illuminating a light positioned behind a stencil that outlines the shape of the message. In some contemplated embodiments, the night light is integrated into the grip handle coupled to the upper frame as shown in FIG. 36 and lights up the grip to indicate the status of the person support apparatus.

Figure 17:
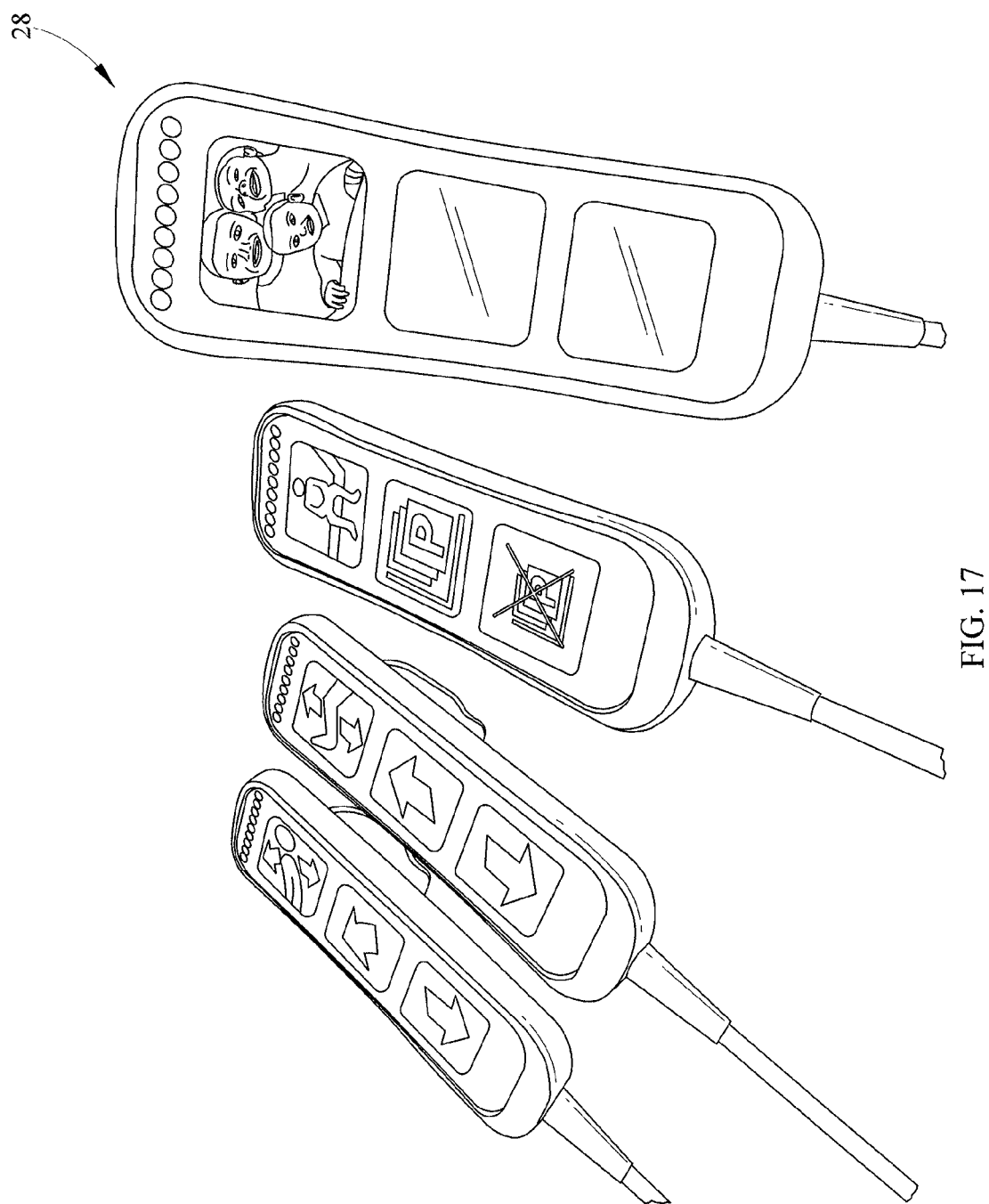
FIG. 17 is a pendant according to another contemplated embodiment of the current disclosure including screen keys.
Figure 18:
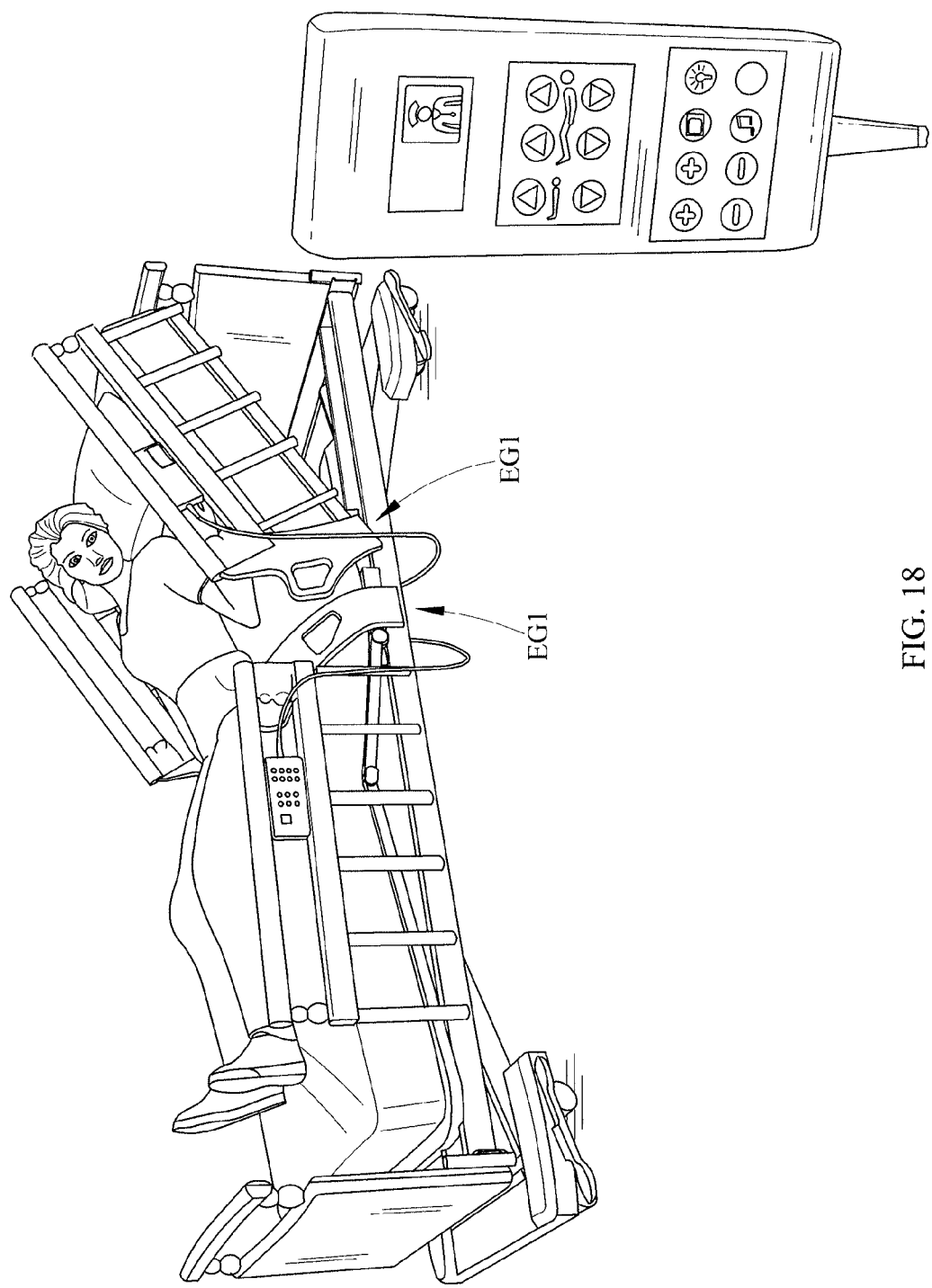
FIG. 18 is a person support apparatus according to another contemplated embodiment of the current disclosure.
Figure 19:
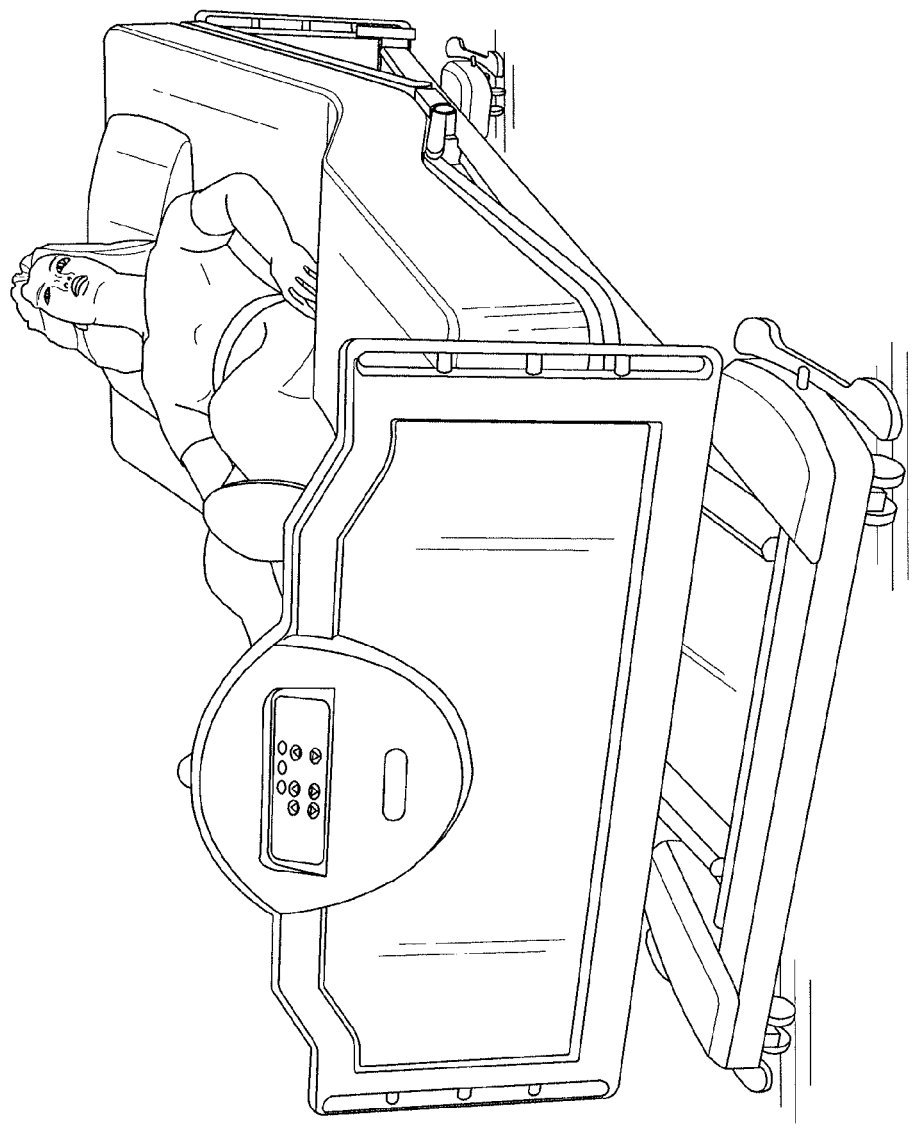
FIG. 19 is a person support apparatus according to another contemplated embodiment of the current disclosure.
Figure 20:
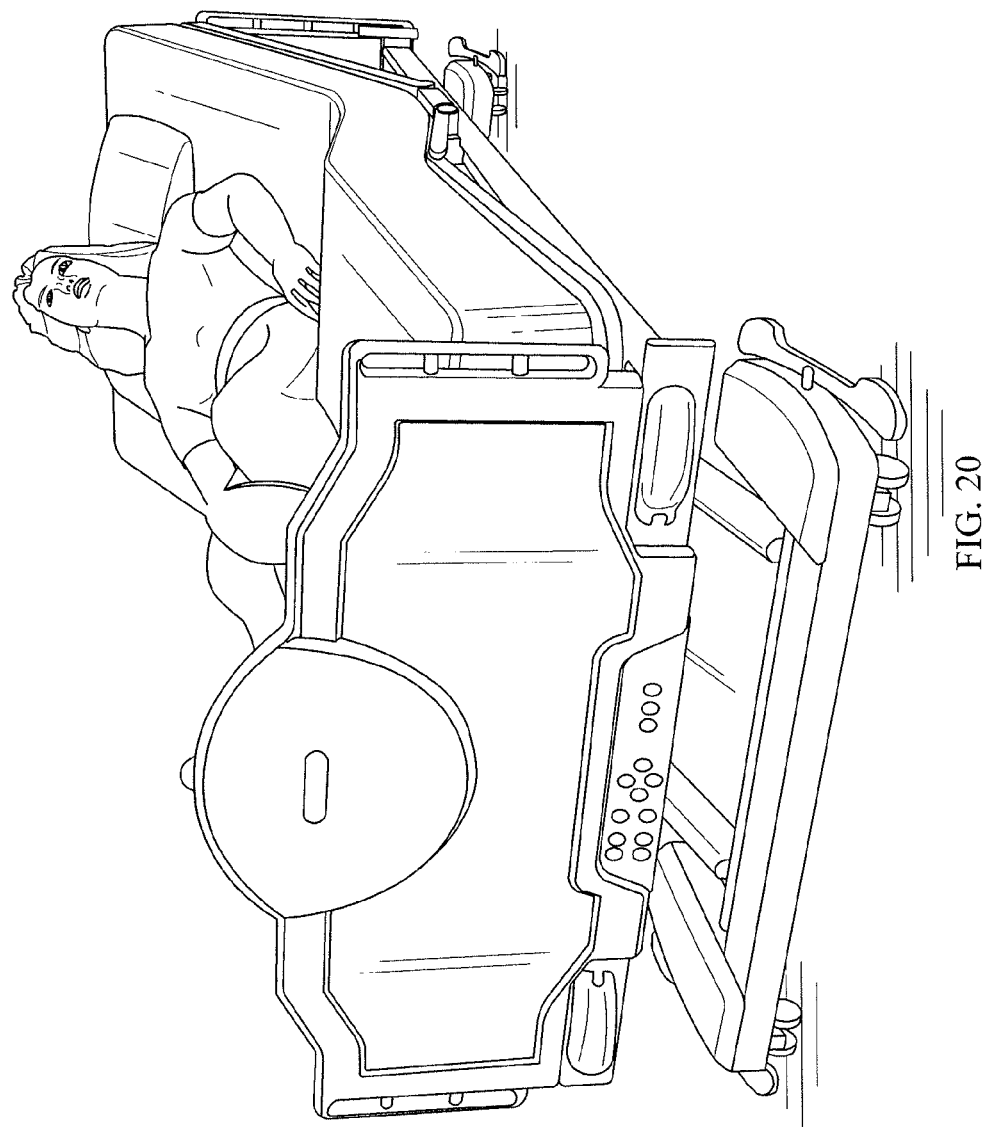
FIG. 20 is a person support apparatus according to another contemplated embodiment of the current disclosure showing status indicating lights coupled to the foot end of the person support apparatus.
Figure 24:
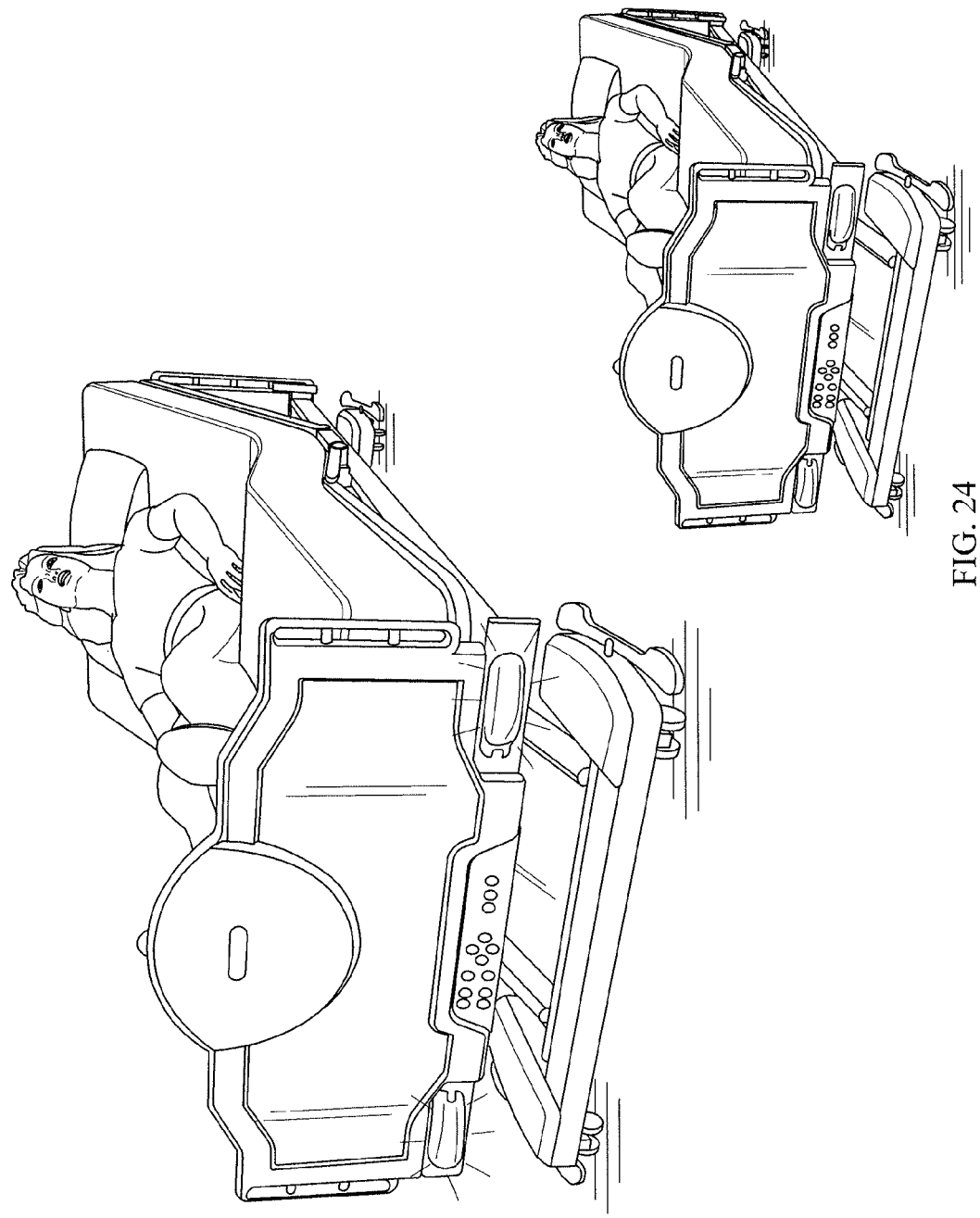
FIG. 24 is the status indicating lights of FIG. 20 according to another contemplated embodiment of the current disclosure.
Figure 25:
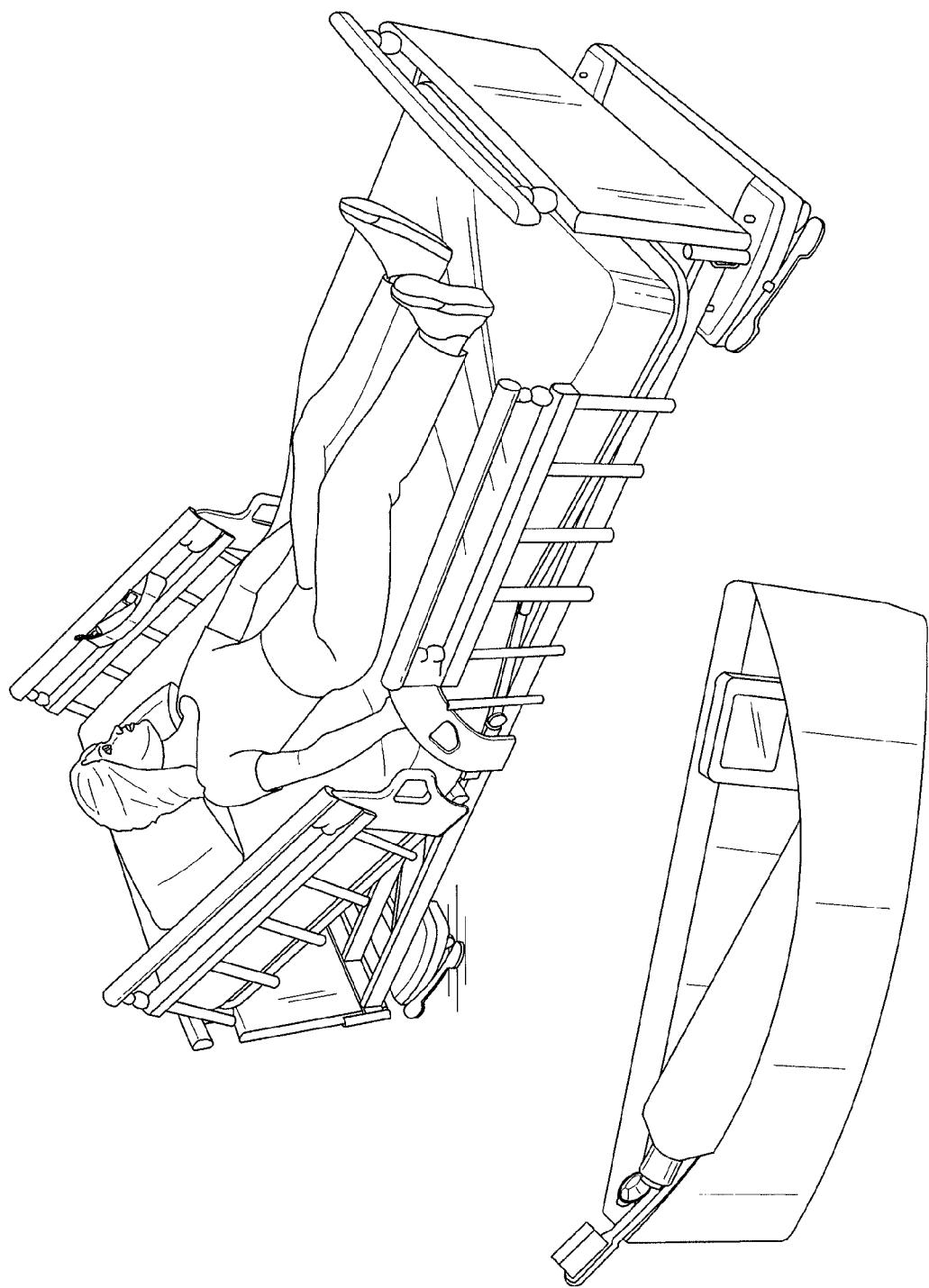
FIG. 25 is a person support apparatus according to another contemplated embodiment of the current disclosure showing a storage area for storing personal items configured to be coupled to a siderail.
Figure 26:
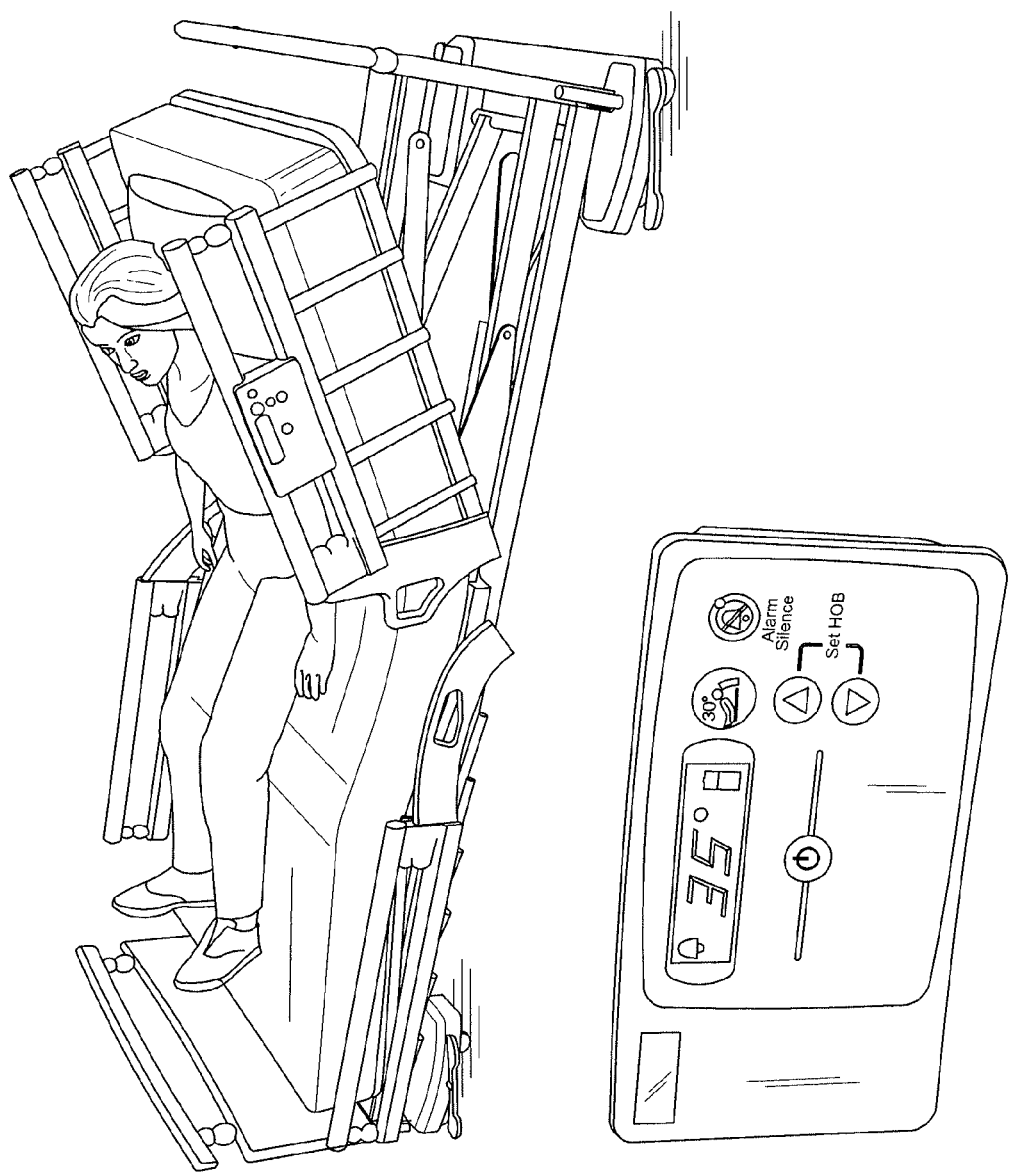
FIG. 26 is a person support apparatus according to another contemplated embodiment of the current disclosure showing a pendant configured to be coupled to the siderail of the person support apparatus and configured to digitally display the angle of the head end of the bed with respect to horizontal and alarm when the angle drops below a predetermined threshold.
Figure 27:
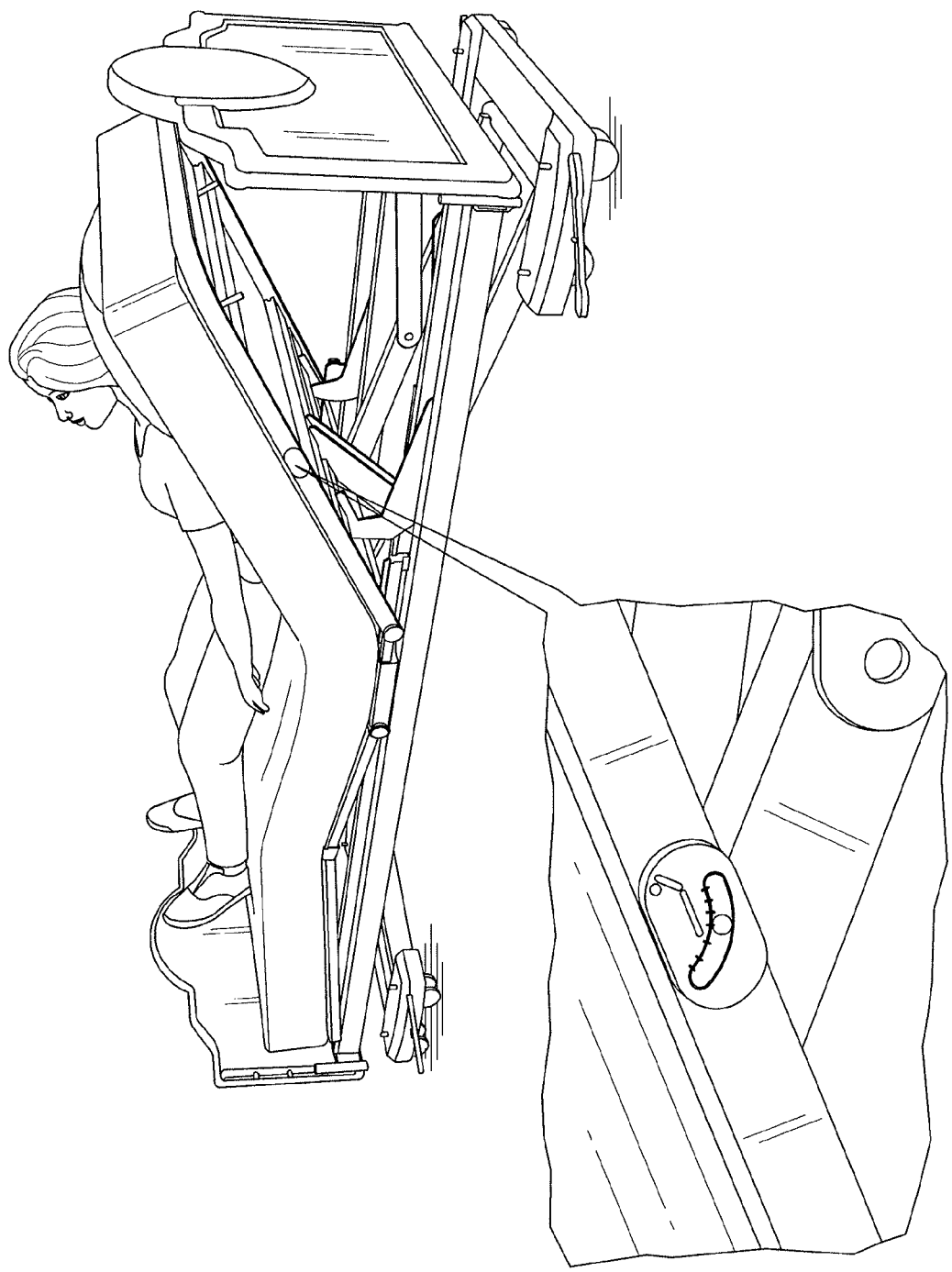
FIG. 27 is a person support apparatus according to another contemplated embodiment of the current disclosure showing an inclinometer coupled to the upper frame with a rolling element configured to move within a housing to indicate the angle of the head end of the bed with respect to horizontal.
Figure 28:
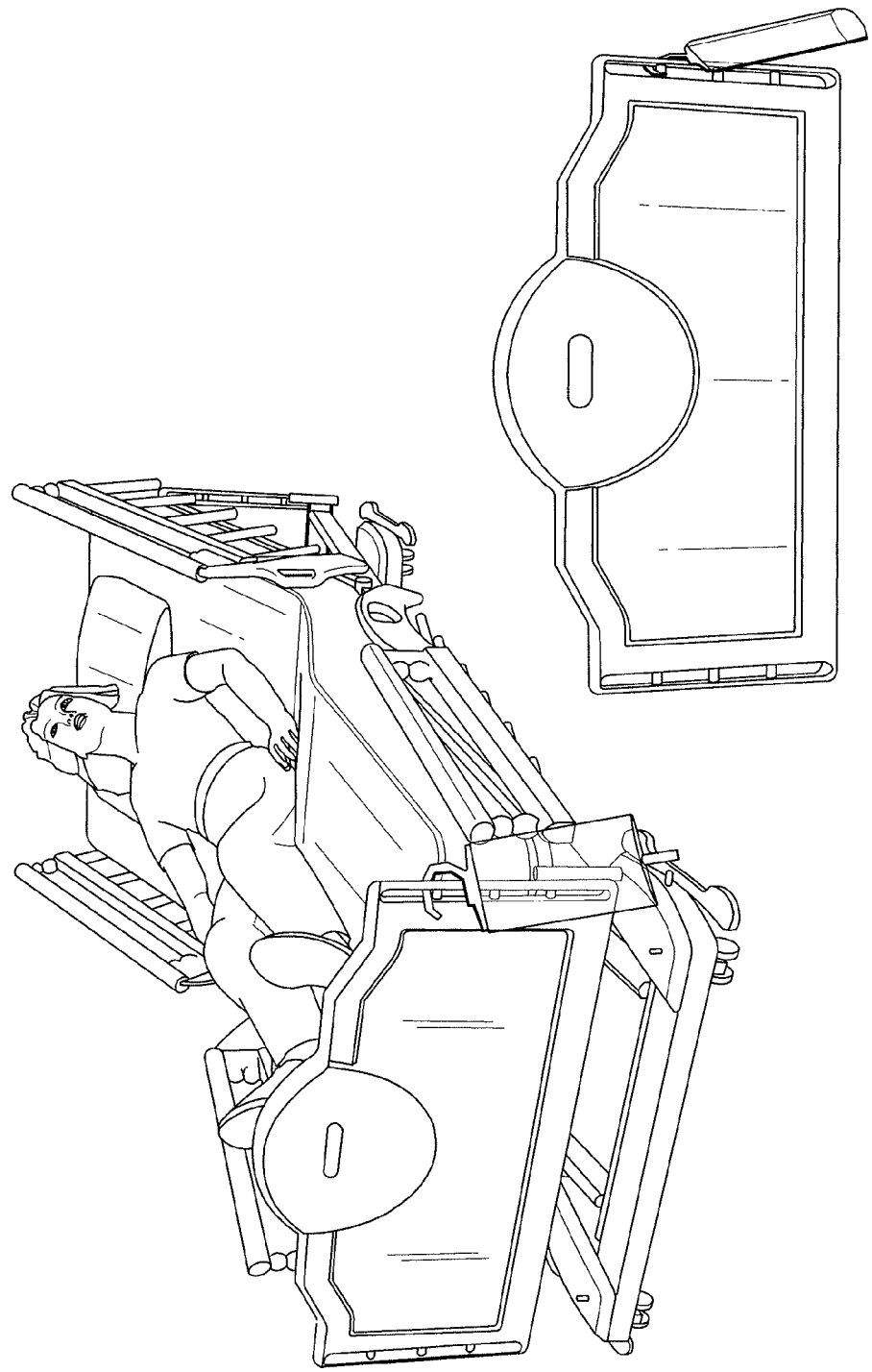
FIG. 28 is a person support apparatus according to another contemplated embodiment of the current disclosure.

The pendant 28 is configured to control at least one function of the person support apparatus 10. In one illustrative embodiment, the pendant 28 includes high resolution, full color displays, such as, TFT ScreenKeys, which can display images thereon that the user can press to select the function they wish the bed to perform as shown in FIG. 17. The ScreenKeys, which can feature 128*128 pixel resolution, an SPI interface, full color imaging, bitmap addressable—high level commands, internal character generation, 7 lines with 9 characters per line, user downloadable font support, 10 fps refresh rate, and low profile, among other things. The user can select different modes on the controller pressing the top key TK1, which changes the mode indicator MI1 and the two bottom keys BK1 or action keys BK1 to control different functions of the person support apparatus 10. In some contemplated embodiments, the keys display an image of a family member of the patient to make the pendant seem less intimidating.

The control system CS1 is electrically coupled to the night-light 27, the pendant 28, the lift system 14, and an input device ID1. The control system CS1 includes a processor PR1 and memory ME1 that stores instructions to be executed by the processor PR1. The input device ID1 is configured to provide an input corresponding to the status of the person support apparatus 10, such as, for example, whether the upper frame is at a predetermined egress height. In some contemplated embodiments, the input device ID1 is an electronic medical record system that displays messages to the occupant or caregiver to remind them to perform actions or seek assistance before performing actions. In another contemplated embodiment, the input device is a remote caregiver station that allows the caregiver to provide information to the occupant remotely, such as, asking the occupant to remain in bed until a nurse can assist them with exiting the person support apparatus. In yet another contemplated embodiment, the input device is a sensor that, in one example, senses the distance between the upper frame and the floor. In some contemplated embodiments, the control system controls the operation of the night light to display messages on the floor in accordance with the input from the input device.

Any theory, mechanism of operation, proof, or finding stated herein is meant to further enhance understanding of principles of the present disclosure and is not intended to make the present disclosure in any way dependent upon such theory, mechanism of operation, illustrative embodiment, proof, or finding. It should be understood that while the use of the word preferable, preferably or preferred in the description above indicates that the feature so described can be more desirable, it nonetheless can not be necessary and embodiments lacking the same can be contemplated as within the scope of the disclosure, that scope being defined by the claims that follow.

In reading the claims it is intended that when words such as "a," "an," "at least one," "at least a portion" are used there is no intention to limit the claim to only one item unless specifically stated to the contrary in the claim. When the language "at least a portion" and/or "a portion" is used the item can include a portion and/or the entire item unless specifically stated to the contrary.

It should be understood that only selected embodiments have been shown and described and that all possible alternatives, modifications, aspects, combinations, principles, variations, and equivalents that come within the spirit of the disclosure as defined herein or by any of the following claims are desired to be protected. While embodiments of the disclosure have been illustrated and described in detail in the drawings and foregoing description, the same are to be considered as illustrative and not intended to be exhaustive or to limit the disclosure to the precise forms disclosed. Additional alternatives, modifications and variations can be apparent to those skilled in the art. Also, while multiple inventive aspects and principles can have been presented, they need not be utilized in combination, and various combinations of inventive aspects and principles are possible in light of the various embodiments provided above.

What is claimed is:

1. An information communication system for a person support apparatus, comprising:
   an input device;
   a first indicator configured to emit light toward a surface;
   a second indicator coupled to a grip of a handle coupled to the person support apparatus; and
   a controller configured to control operation of the first and second indicators as a function of an input from the input device, wherein the controller causes the first indicator to display a message to inform the occupant as to when they should egress from the patient support apparatus, wherein the input is indicative of a status of the person support apparatus, wherein the controller signals the second indicator to illuminate when the first indicator displays the message, wherein the handle includes a first tubular portion that extends generally vertically upwardly beyond an upper surface of a mattress of the person support apparatus and the grip extends away from an upper end of the first tubular portion, wherein light from the second indicator is emitted from the grip but not from the first tubular portion such that light is emitted from the grip generally upwardly and away from the first tubular portion.

2. The information communication system of claim 1, wherein the message includes at least one character.

3. The information communication system of claim 1, wherein the message includes a symbol.

4. The information communication system of claim 3, wherein the message includes a circle with a backward slash passing through the circle.

5. The information communication system of claim 3, wherein the symbol includes a triangle with an exclamation point positioned within the triangle.

6. The information communication system of claim 1, wherein the message is displayed in a plurality of colors.

7. The information communication system of claim 1, wherein a message indicating caution is displayed in amber light.

8. The information communication system of claim 1, wherein a message indicating that a user may proceed with an action is displayed in green light.

9. The information communication system of claim 1, wherein the message indicating an unsatisfactory condition is displayed in red light.

10. The information communication system of claim 1, wherein the light emitted by the first indicator is filtered so that the light passing through excludes the shape of the message.

11. The information communication system of claim 1, wherein the light emitted by the first indicator is filtered so that the light passing through includes the shape of the message.

12. The information communication system of claim 1, wherein the message indicates to the user when the person support apparatus is at a predetermined egress height.

13. The information communication system of claim 1, wherein the message includes an image of a nurse call icon.

14. The information communication system of claim 1, wherein the first indicator is coupled to an upper frame of the person support apparatus.

15. The information communication system of claim 1, wherein the light emitted by the first indicator is directed toward a floor adjacent to a side of the person support apparatus.

16. The information communication system of claim 1, wherein the message includes a status of the person support apparatus.

17. An indicating system, comprising:
an input device;
a first indicator coupled to a person support apparatus and configured to emit light toward a surface, the light causing a message to be displayed on the surface;
a second indicator coupled to a grip of a handle coupled to the person support apparatus; and
a control system configured to receive an input from the input device and control the operation of the first and second indicators as a function of the input, the input being indicative of a status of a person support apparatus, wherein the control system signals the second indicator to illuminate when the first indicator displays the message, wherein the handle includes a first tubular portion that extends generally vertically upwardly beyond an upper surface of a mattress of the person support apparatus and the grip extends away from an upper end of the first tubular portion, wherein light from the second indicator is emitted from the grip but not from the first tubular portion such that light is emitted from the grip generally upwardly and away from the first tubular portion.

18. The indicating system of claim 17, wherein the message informs an occupant when to egress from the person support apparatus.

19. The indicating system of claim 17, wherein the message includes at least one of a character and a symbol.

* * * * *